(12) United States Patent
Lee et al.

(10) Patent No.: US 12,655,215 B2
(45) Date of Patent: Jun. 16, 2026

(54) ANTI-OSCAR ANTIBODY FOR PREVENTING OR TREATING OSTEOARTHRITIS

(71) Applicant: EWHA UNIVERSITY—INDUSTRY COLLABORATION FOUNDATION, Seoul (KR)

(72) Inventors: Soo Young Lee, Seoul (KR); Hyunbo Shim, Seoul (KR); Du-ri Park, Seoul (KR)

(73) Assignee: EWHA UNIVERSITY-INDUSTRY COLLABORATION FOUNDATION, Seoul (KR)

( * ) Notice: Subject to any disclaimer, the term of this patent is extended or adjusted under 35 U.S.C. 154(b) by 847 days.

(21) Appl. No.: 17/998,642

(22) PCT Filed: Jun. 1, 2020

(86) PCT No.: PCT/KR2020/007086
§ 371 (c)(1),
(2) Date: Nov. 11, 2022

(87) PCT Pub. No.: WO2020/246760
PCT Pub. Date: Dec. 10, 2020

(65) Prior Publication Data
US 2023/0399397 A1 Dec. 14, 2023

(30) Foreign Application Priority Data

Jun. 4, 2019 (KR) ........................ 10-2019-0066154
May 29, 2020 (KR) ........................ 10-2020-0064933

(51) Int. Cl.
| | |
|---|---|
| C07K 16/28 | (2006.01) |
| A61K 39/00 | (2006.01) |
| A61P 19/02 | (2006.01) |
| G01N 33/50 | (2006.01) |

(52) U.S. Cl.
CPC .......... C07K 16/2803 (2013.01); A61K 39/00 (2013.01); A61P 19/02 (2018.01); G01N 33/5044 (2013.01); A61K 2039/505 (2013.01); C07K 2317/622 (2013.01); C07K 2317/76 (2013.01); C07K 2317/92 (2013.01); G01N 2333/96494 (2013.01); G01N 2800/105 (2013.01)

(58) Field of Classification Search
None
See application file for complete search history.

(56) References Cited

U.S. PATENT DOCUMENTS

| | | | |
|---|---|---|---|
| 9,488,646 | B2 | 11/2016 | Cook et al. |
| 2009/0239804 | A1 | 9/2009 | Wang |
| 2014/0056918 | A1 | 2/2014 | Guo et al. |
| 2017/0030925 | A1 | 2/2017 | Cook et al. |

FOREIGN PATENT DOCUMENTS

| | | |
|---|---|---|
| WO | WO 2013/011063 A1 | 1/2013 |
| WO | WO 2016/019225 A1 | 2/2016 |
| WO | WO 2017/123642 A1 | 7/2017 |

OTHER PUBLICATIONS

Extended European Search Report issued in European Patent Application No. 20817860.8, dated Apr. 11, 2025.
Kim, G. M. et al., "Development of Anti-OSCAR Antibodies for the Treatment of Osteoarthritis," *Biomedicines*, 11.2844 (2023): 1-16.
Bai, X. et al., "A Novel Human scFv Library with Non-Combinatorial Synthetic CDR Diversity," *PLOS ONE*, DOI.10.1371 (2015): 1-18.
Kim, N. et al., "A Novel Member of the Leukocyte Receptor Complex Regulates Osteoclast Differentiation," *J. Exp. Med.*, 195.2 (2002): 201-209.
Schultz, H. S. et al., "OSCAR-collagen signaling in monocytes plays a proinflammatory role and may contribute to the pathogenesis of rheumatoid arthritis," *European Journal of Immunology*, 46 (2016): 952-963.
Yang, H. Y. et al., "Construction of a Large Synthetic Human scFv Library with Six Diversified CDRs and High Functional Diversity," *Mol. Cells*, 27 (2009): 225-235.

*Primary Examiner* — Gary B Nickol
(74) *Attorney, Agent, or Firm* — pH IP Law

(57) ABSTRACT

The present application relates to a composition for preventing or treating osteoarthritis, including an osteoclast-associated Ig-like receptor (OSCAR) protein inhibitor, a polynucleotide encoding an anti-OSCAR antibody or a fragment thereof, and an OSCAR protein inhibitor screening method. According to embodiments of the present application, the anti-osteoclast-associated Ig-like receptor (OSCAR) antibody or a fragment thereof of the present application may prevent or treat osteoarthritis through a mechanism for inhibiting the OSCAR-collagen interaction in chondrocytes, and an OSCAR protein inhibitor having an excellent effect of inhibiting the OSCAR-collagen interaction can be screened by using the OSCAR protein inhibitor screening method of the present application.

3 Claims, 8 Drawing Sheets
Specification includes a Sequence Listing.

FIGS. 3A-C
FIGS. 4A-C
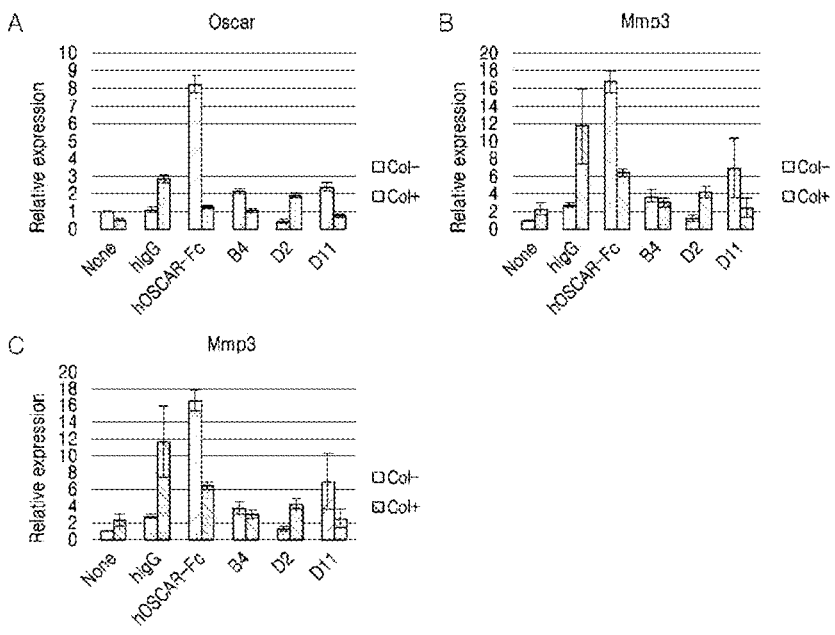

FIGS. 7A-B (A)

```
Parental CDR-H3 ----- CAKOOOOOOOFDI ------ ⎫
       D11-H3-1 ----- CAKXXOOOOOFDI ----    ⎪
       D11-H3-2 ----- CAKOXXOOOOFDI ---     ⎪
       D11-H3-3 ----- CAKOOXXOOOFDI ----    ⎬  2-AA scanning
       D11-H3-4 ----- CAKOOOXXOOFDI ----    ⎪     random
       D11-H3-5 ----- CAKOOOOXXOFDI ------  ⎪    mutagenesis
       D11-H3-6 ----- CAKOOOOOXXFDI ---     ⎭
```

(B)

| lib | D11-H3-1 | | D11-H3-2 | | D11-H3-3 | | D11-H3-4 | | D11-H3-5 | | D11-H3-6 | |
|---|---|---|---|---|---|---|---|---|---|---|---|---|
| | input | output | input | output | input | output | input | output | input | output | input | output |
| 1st | 3.2e10 | 0 | 1.5e10 | 0 | 5.6e10 | 7.0e4 | 1.8e10 | 3.0e4 | 1.9e10 | 2.0e4 | 7.0e10 | 4.0e4 |
| 2nd | 5.0e10 | 1.6e6 | 1.6e11 | 6.2e6 | 3.9e11 | 3.1e7 | 1.9e11 | 2.6e7 | 2.6e11 | 2.0e7 | 5.1e11 | 1.2e7 |
| 3rd | 1.5e12 | 1.4e7 | 3.0e11 | 2.4e7 | 2.7e17 | 0 | 4.0e11 | 3.8e6 | 4.6e11 | 2.0e6 | 2.3e11 | 2.0e5 |

FIGS. 9A-B
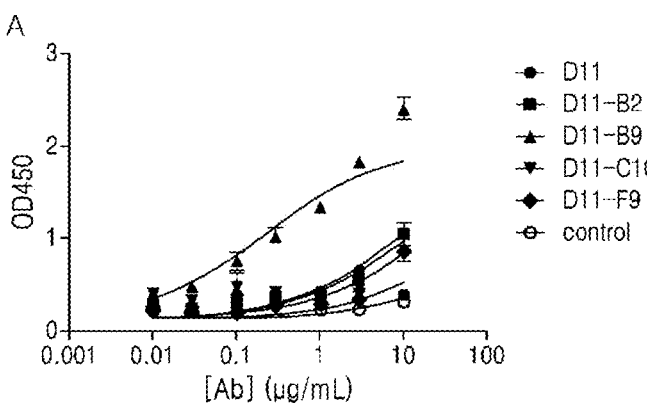
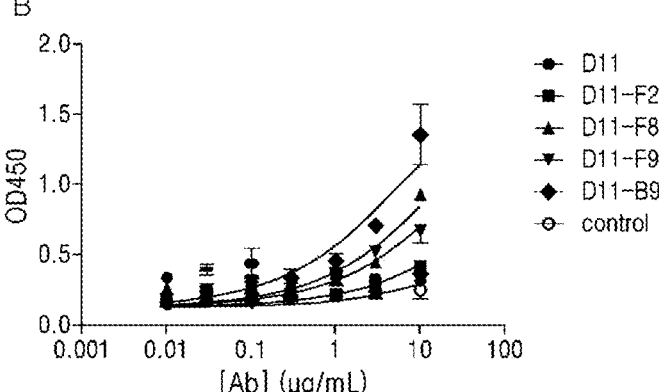

FIG. 10

FIGS. 11A-B
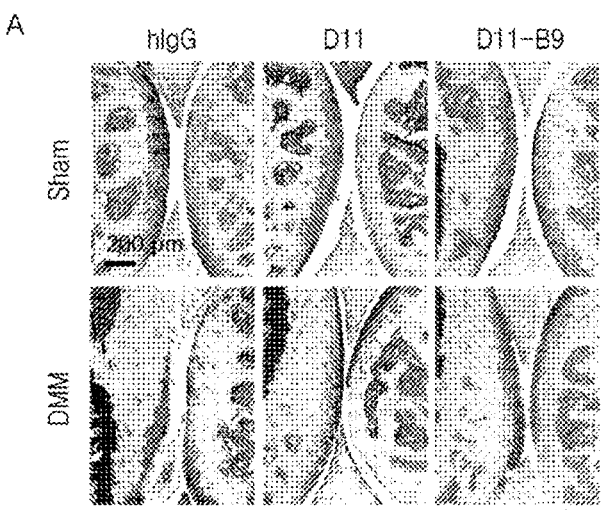
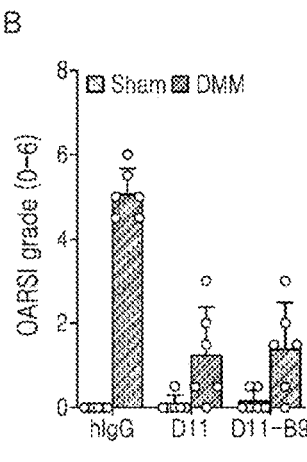
FIGS.12A-C
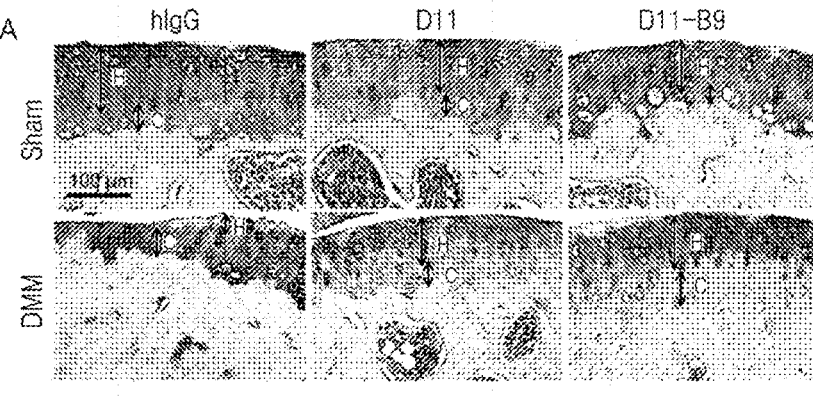
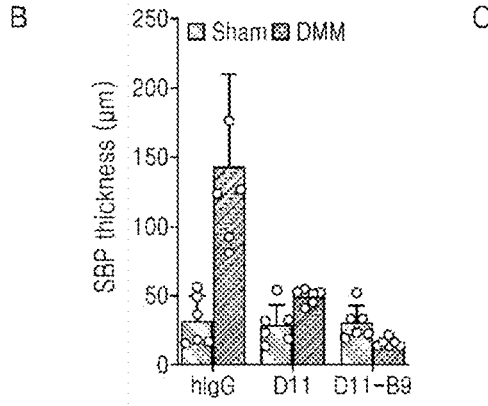
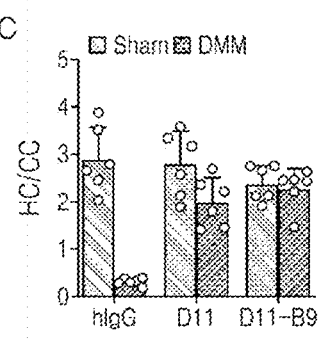

FIGS. 13A-C
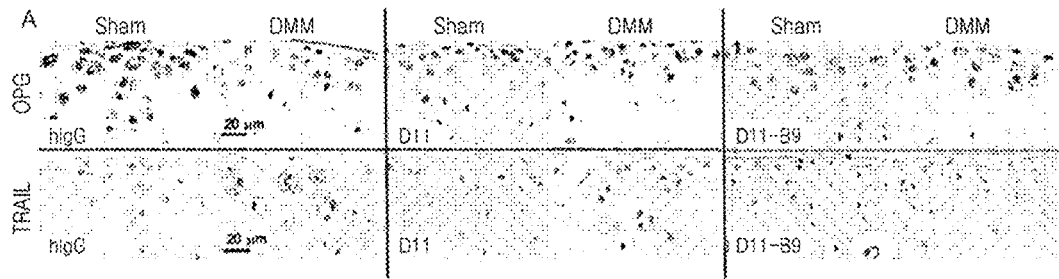
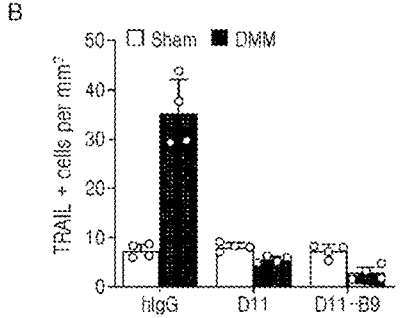
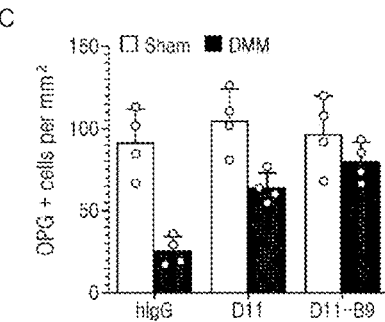
FIGS.14A-B
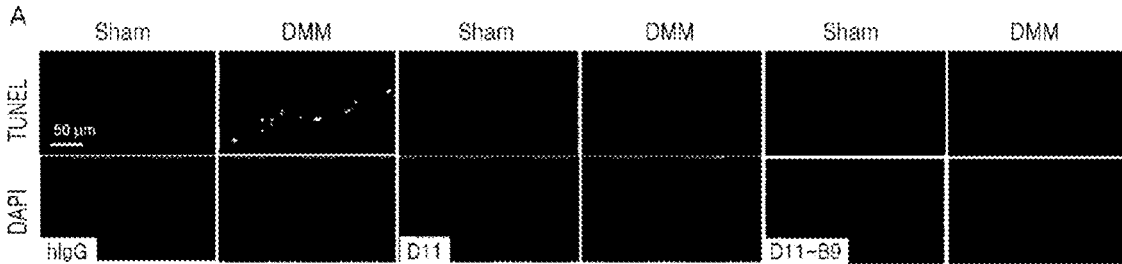
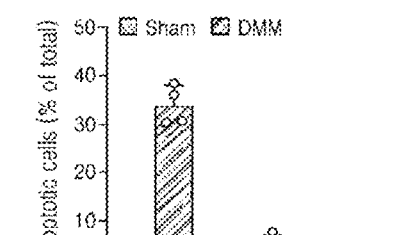

SEQUENCE LISTING

<160> NUMBER OF SEQ ID NOS: 29

<210> SEQ ID NO 1
<211> LENGTH: 19
<212> TYPE: DNA
<213> ORGANISM: Artificial Sequence
<220> FEATURE:
<223> OTHER INFORMATION: pC3X-f

<400> SEQUENCE: 1
gcacgacagg tttcccgac                                                              19

<210> SEQ ID NO 2
<211> LENGTH: 20
<212> TYPE: DNA
<213> ORGANISM: Artificial Sequence
<220> FEATURE:
<223> OTHER INFORMATION: pC3X-b

<400> SEQUENCE: 2
aaccatcgat agcagcaccg                                                             20

<210> SEQ ID NO 3
<211> LENGTH: 22
<212> TYPE: DNA
<213> ORGANISM: Artificial Sequence
<220> FEATURE:
<223> OTHER INFORMATION: ompseq

<400> SEQUENCE: 3
aagacagcta tcgcgattgc ag                                                          22

<210> SEQ ID NO 4
<211> LENGTH: 477
<212> TYPE: PRT
<213> ORGANISM: Artificial Sequence
<220> FEATURE:
<223> OTHER INFORMATION: hOSCAR-Fc

<400> SEQUENCE: 4

Met Glu Thr Asp Thr Leu Leu Leu Trp Val Leu Leu Leu Trp Val Pro
1               5                   10                  15

Gly Ser Thr Gly Asp Ile Thr Pro Ser Val Ala Ile Ile Val Pro Pro
            20                  25                  30

Ala Ser Tyr His Pro Lys Pro Trp Leu Gly Ala Gln Pro Ala Thr Val
        35                  40                  45

Val Thr Pro Gly Val Asn Val Thr Leu Arg Cys Arg Ala Pro Gln Pro
    50                  55                  60

Ala Trp Arg Phe Gly Leu Phe Lys Pro Gly Glu Ile Ala Pro Leu Leu
65                  70                  75                  80

Phe Arg Asp Val Ser Ser Glu Leu Ala Glu Phe Phe Leu Glu Glu Val
                85                  90                  95

Thr Pro Ala Gln Gly Gly Ser Tyr Arg Cys Cys Tyr Arg Arg Pro Asp
            100                 105                 110

Trp Gly Pro Gly Val Trp Ser Gln Pro Ser Asp Val Leu Glu Leu Leu
        115                 120                 125

Val Thr Glu Glu Leu Pro Arg Pro Ser Leu Val Ala Leu Pro Gly Pro
    130                 135                 140

Val Val Gly Pro Gly Ala Asn Val Ser Leu Arg Cys Ala Gly Arg Leu
145                 150                 155                 160

Arg Asn Met Ser Phe Val Leu Tyr Arg Glu Gly Val Ala Ala Pro Leu

-continued

```
              165            170            175

Gln Tyr Arg His Ser Ala Gln Pro Trp Ala Asp Phe Thr Leu Leu Gly
            180            185            190

Ala Arg Ala Pro Gly Thr Tyr Ser Cys Tyr Tyr His Thr Pro Ser Ala
            195            200            205

Pro Tyr Val Leu Ser Gln Arg Ser Glu Val Leu Val Ile Ser Trp Glu
            210            215            220

Asp Ser Gly Ser Ser Asp Tyr Thr Arg Gly Asn Leu Val Arg Leu Gly
225            230            235            240

Leu Ala Gly Leu Val Gly Gln Ala Gly Gln Glu Pro Lys Ser Ser Asp
            245            250            255

Lys Thr His Thr Cys Pro Pro Cys Pro Ala Pro Glu Leu Leu Gly Gly
            260            265            270

Pro Ser Val Phe Leu Phe Pro Pro Lys Pro Lys Asp Thr Leu Met Ile
            275            280            285

Ser Arg Thr Pro Glu Val Thr Cys Val Val Val Asp Val Ser His Glu
            290            295            300

Asp Pro Glu Val Lys Phe Asn Trp Tyr Val Asp Gly Val Glu Val His
305            310            315            320

Asn Ala Lys Thr Lys Pro Arg Glu Glu Gln Tyr Asn Ser Thr Tyr Arg
            325            330            335

Val Val Ser Val Leu Thr Val Leu His Gln Asp Trp Leu Asn Gly Lys
            340            345            350

Glu Tyr Lys Cys Lys Val Ser Asn Lys Ala Leu Pro Ala Pro Ile Glu
            355            360            365

Lys Thr Ile Ser Lys Ala Lys Gly Gln Pro Arg Glu Pro Gln Val Tyr
            370            375            380

Thr Leu Pro Pro Ser Arg Asp Glu Leu Thr Lys Asn Gln Val Ser Leu
385            390            395            400

Thr Cys Leu Val Lys Gly Phe Tyr Pro Ser Asp Ile Ala Val Glu Trp
            405            410            415

Glu Ser Asn Gly Gln Pro Glu Asn Asn Tyr Lys Thr Thr Pro Pro Val
            420            425            430

Leu Asp Ser Asp Gly Ser Phe Phe Leu Tyr Ser Lys Leu Thr Val Asp
            435            440            445

Lys Ser Arg Trp Gln Gln Gly Asn Val Phe Ser Cys Ser Val Met His
            450            455            460

Glu Ala Leu His Asn His Tyr Thr Gln Lys Ser Leu Ser
465            470            475

<210> SEQ ID NO 5
<211> LENGTH: 462
<212> TYPE: PRT
<213> ORGANISM: Artificial Sequence
<220> FEATURE:
<223> OTHER INFORMATION: mOSCAR-Fc

<400> SEQUENCE: 5

Met Glu Thr Asp Thr Leu Leu Leu Trp Val Leu Leu Leu Trp Val Pro
1               5               10              15

Gly Ser Thr Gly Asp Phe Thr Pro Thr Ala Pro Leu Ala Ser Tyr Pro
                20              25              30

Gln Pro Trp Leu Gly Ala His Pro Ala Ala Val Val Thr Pro Gly Ile
            35              40              45

Asn Val Thr Leu Thr Cys Arg Ala Pro Gln Ser Ala Trp Arg Phe Ala
```

-continued

```
        50              55              60

Leu Phe Lys Ser Gly Leu Val Thr Pro Leu Leu Leu Arg Asp Val Ser
65              70              75              80

Val Glu Leu Ala Glu Phe Phe Leu Glu Glu Val Thr Pro Ala Gln Gly
                85              90              95

Gly Ser Tyr His Cys Arg Tyr Arg Lys Thr Asp Trp Gly Pro Gly Val
            100             105             110

Trp Ser Gln Pro Ser Asn Val Leu Glu Leu Leu Val Thr Asp Gln Leu
            115             120             125

Pro Arg Pro Ser Leu Val Ala Leu Pro Gly Pro Val Val Ala Pro Gly
        130             135             140

Ala Asn Val Ser Leu Arg Cys Ala Gly Arg Ile Pro Gly Met Ser Phe
145             150             155             160

Ala Leu Tyr Arg Val Gly Val Ala Thr Pro Leu Gln Tyr Ile Asp Ser
            165             170             175

Val Gln Pro Trp Ala Asp Phe Leu Leu Ile Gly Thr His Thr Pro Gly
            180             185             190

Thr Tyr Cys Cys Tyr Tyr His Thr Pro Ser Ala Pro Tyr Val Leu Ser
            195             200             205

Gln Arg Ser Gln Pro Leu Val Ile Ser Phe Glu Gly Ser Gly Ser Leu
        210             215             220

Asp Tyr Thr Gln Gly Asn Gly Gln Ala Gly Gln Glu Pro Lys Ser Ser
225             230             235             240

Asp Lys Thr His Thr Cys Pro Pro Cys Pro Ala Pro Glu Leu Leu Gly
            245             250             255

Gly Pro Ser Val Phe Leu Phe Pro Pro Lys Pro Lys Asp Thr Leu Met
            260             265             270

Ile Ser Arg Thr Pro Glu Val Thr Cys Val Val Val Asp Val Ser His
            275             280             285

Glu Asp Pro Glu Val Lys Phe Asn Trp Tyr Val Asp Gly Val Glu Val
        290             295             300

His Asn Ala Lys Thr Lys Pro Arg Glu Glu Gln Tyr Asn Ser Thr Tyr
305             310             315             320

Arg Val Val Ser Val Leu Thr Val Leu His Gln Asp Trp Leu Asn Gly
            325             330             335

Lys Glu Tyr Lys Cys Lys Val Ser Asn Lys Ala Leu Pro Ala Pro Ile
            340             345             350

Glu Lys Thr Ile Ser Lys Ala Lys Gly Gln Pro Arg Glu Pro Gln Val
            355             360             365

Tyr Thr Leu Pro Pro Ser Arg Asp Glu Leu Thr Lys Asn Gln Val Ser
        370             375             380

Leu Thr Cys Leu Val Lys Gly Phe Tyr Pro Ser Asp Ile Ala Val Glu
385             390             395             400

Trp Glu Ser Asn Gly Gln Pro Glu Asn Asn Tyr Lys Thr Thr Pro Pro
            405             410             415

Val Leu Asp Ser Asp Gly Ser Phe Phe Leu Tyr Ser Lys Leu Thr Val
            420             425             430

Asp Lys Ser Arg Trp Gln Gln Gly Asn Val Phe Ser Cys Ser Val Met
            435             440             445

His Glu Ala Leu His Asn His Tyr Thr Gln Lys Ser Leu Ser
        450             455             460
```

<210> SEQ ID NO 6

-continued

```
<211> LENGTH: 116
<212> TYPE: PRT
<213> ORGANISM: Artificial Sequence
<220> FEATURE:
<223> OTHER INFORMATION: B4_VH_AA

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Tyr His Gly Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Pro Asp Glu Phe Asp Tyr Trp Gly Gln Gly Thr Leu Val
            100                 105                 110

Thr Val Ser Ser
        115

<210> SEQ ID NO 7
<211> LENGTH: 110
<212> TYPE: PRT
<213> ORGANISM: Artificial Sequence
<220> FEATURE:
<223> OTHER INFORMATION: B4_VL_AA

<400> SEQUENCE: 7

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asn Ser His Arg Pro Ser Gly Val Pro Asp Arg Phe Ser
    50                  55                  60

Gly Ser Lys Pro Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Asn Gly Tyr Val Phe Gly Gly Gly Thr Lys Leu Thr Val Leu
            100                 105                 110

<210> SEQ ID NO 8
<211> LENGTH: 446
<212> TYPE: PRT
<213> ORGANISM: Artificial Sequence
<220> FEATURE:
<223> OTHER INFORMATION: B4_IGG-H_AA

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

-continued

```
Ala Met Ser Trp Val Arg Gln Ala Pro Gly Lys Gly Leu Glu Trp Val
    35                  40                  45

Ser Gly Ile Tyr His Gly Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Pro Asp Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

-continued

```
<210> SEQ ID NO 9
<211> LENGTH: 216
<212> TYPE: PRT
<213> ORGANISM: Artificial Sequence
<220> FEATURE:
<223> OTHER INFORMATION: B4_IGG-L_AA

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ser Val Thr Trp Tyr Gln Gln Leu Pro Gly Thr Ala Pro Lys Leu Leu
        35                  40                  45

Ile Tyr Tyr Asn Ser His Arg Pro Ser Gly Val Pro Asp Arg Phe Ser
    50                  55                  60

Gly Ser Lys Pro Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Asn Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 10
<211> LENGTH: 348
<212> TYPE: DNA
<213> ORGANISM: Artificial Sequence
<220> FEATURE:
<223> OTHER INFORMATION: B4_VH_NT

<400> SEQUENCE: 10
gaggtgcagc tgttggagtc tgggggaggc ttggtacagc ctggggggtc cctgagactc      60
tcctgtgcag cctctggatt cacctttagc gattatgcta tgagctgggt ccgccaggct     120
ccagggaagg ggctggagtg ggtctcaggg atctatcatg gtggtggtaa tatatattac     180
gctgattctg taaaaggtcg gttcaccatc tccagagaca attccaagaa cacgctgtat     240
ctgcaaatga acagcctgag agccgaggac acggccgtgt attactgtgc gagagctcct     300
gatgagttcg actactgggg ccagggtaca ctagtcaccg tgagctca                  348

<210> SEQ ID NO 11
<211> LENGTH: 330
<212> TYPE: DNA
<213> ORGANISM: Artificial Sequence
<220> FEATURE:
```

<223> OTHER INFORMATION: B4_VL_NT

<400> SEQUENCE: 11

```
cagtctgtgc tgactcagcc accctcagcg tctgggaccc ccgggcagag ggtcaccatc        60
tcttgtagtg gctcttcatc taatattggc aataattctg tcacctggta ccagcagctc       120
ccaggaacgg cccccaaact cctcatctat tataatagtc atcggccaag cggggtccct       180
gaccgattct ctggctccaa gcctggcacc tcagcctccc tggccatcag tgggctccgg       240
tccgaggatg aggctgatta ttactgtggt gcttgggatt ctagcctgaa tggttatgtc       300
ttcggcggag gcaccaagct gacggtccta                                        330
```

```
<210> SEQ ID NO 12
<211> LENGTH: 1338
<212> TYPE: DNA
<213> ORGANISM: Artificial Sequence
<220> FEATURE:
<223> OTHER INFORMATION: B4_IGG-H_NT
```

<400> SEQUENCE: 12

```
gaggtgcagc tgttggagtc tggggggaggc ttggtacagc ctggggggtc cctgagactc        60
tcctgtgcag cctctggatt caccttagc gattatgcta tgagctgggt ccgccaggct       120
ccagggaagg ggctggagtg ggtctcaggg atctatcatg gtggtggtaa tatatattac       180
gctgattctg taaaaggtcg gttcaccatc tccagagaca attccaagaa cacgctgtat       240
ctgcaaatga acagcctgag agccgaggac acggccgtgt attactgtgc gagagctcct       300
gatgagttcg actactgggg ccagggtaca ctagtcaccg tgagctcagc tagcaccaag       360
ggcccatcgg tcttcccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca gcccagcaa caccaaggtg gacaagaaag ttgagcccaa atcttgcgac       660
aaaactcaca catgcccacc gtgcccagca cctgaactcc tggggggacc gtcagtcttc       720
ctcttccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cacgtaccgt       900
gtggtcagcg tcctcaccgt cctgcaccag gactggctga atggcaagga gtacaagtgc       960
aaggtctcca acaaagccct cccagccccc atcgagaaaa ccatctccaa agccaaaggg      1020
cagccccgag aaccacaggt gtacaccctg cccccatccc gggatgagct gaccaagaac      1080
caggtcagcc tgacctgcct ggtcaaaggc ttctatccca gcgacatcgc cgtggagtgg      1140
gagagcaatg ggcagccgga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                    1338
```

```
<210> SEQ ID NO 13
<211> LENGTH: 648
<212> TYPE: DNA
<213> ORGANISM: Artificial Sequence
<220> FEATURE:
<223> OTHER INFORMATION: B4_IGG-L_NT
```

<400> SEQUENCE: 13
cagtctgtgc tgactcagcc accctcagcg tctgggaccc ccgggcagag ggtcaccatc          60
tcttgtagtg gctcttcatc taatattggc aataattctg tcacctggta ccagcagctc         120
ccaggaacgg cccccaaact cctcatctat tataatagtc atcggccaag cggggtccct         180
gaccgattct ctggctccaa gcctggcacc tcagcctccc tggccatcag tgggctccgg         240
tccgaggatg aggctgatta ttactgtggt gcttgggatt ctagcctgaa tggttatgtc         300
ttcggcggag gcaccaagct gacggtccta ggtcagccca aggctgcccc ctcggtcacg         360
ctcttcccac cctcctctga ggagcttcaa gccaacaagg ccacactggt gtgtctcata         420
agtgacttct acccgggagc cgtgacagtg gcctggaagg cagatagcag ccccgtcaag         480
gcgggagtgg agaccaccac acctccaaa caaagcaaca caagtacgc ggccagcagc           540 tacctgagcc tgacgcctga gcagtggaag tcccacaaaa gctacagctg ccaggtcacg         600
catgaaggga gcaccgtgga agacagtg gccctgcag aatgctct                          648

<210> SEQ ID NO 14
<211> LENGTH: 118
<212> TYPE: PRT
<213> ORGANISM: Artificial Sequence
<220> FEATURE:
<223> OTHER INFORMATION: D11_VH_AA

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Trp Thr Trp Val Arg Gln Ala Pro Gly Lys Gly Leu Glu Trp Val
        35                  40                  45

Ser Gly Ser Pro Val Phe Gly Ala Ala Asn Tyr Ala Gln Asn Phe Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ala Gly Phe Thr Gly Gly His Phe Asp Ile Trp Gly Gln Gly Thr
            100                 105                 110

Leu Val Thr Val Ser Ser
        115

<210> SEQ ID NO 15
<211> LENGTH: 108
<212> TYPE: PRT
<213> ORGANISM: Artificial Sequence
<220> FEATURE:
<223> OTHER INFORMATION: D11_VL_AA

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asn Arg Phe Ser

```
            50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Ser
                85                  90                  95

Trp Leu Phe Gly Gly Gly Thr Lys Leu Thr Val Leu
            100                 105

<210> SEQ ID NO 16
<211> LENGTH: 448
<212> TYPE: PRT
<213> ORGANISM: Artificial Sequence
<220> FEATURE:
<223> OTHER INFORMATION: D11_IGG-H_AA

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Trp Thr Trp Val Arg Gln Ala Pro Gly Lys Gly Leu Glu Trp Val
            35                  40                  45

Ser Gly Ser Pro Val Phe Gly Ala Ala Asn Tyr Ala Gln Asn Phe Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ala Gly Phe Thr Gly Gly His Phe Asp Ile Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

-continued

```
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 17
<211> LENGTH: 214
<212> TYPE: PRT
<213> ORGANISM: Artificial Sequence
<220> FEATURE:
<223> OTHER INFORMATION: D11_IGG-L_AA

<400> SEQUENCE: 17

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Gly Asn Ser Asn Arg Pro Ser Gly Val Pro Asn Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Ser
                85                  90                  95

Trp Leu Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
            195                 200                 205

Ala Pro Ala Glu Cys Ser
    210
```

-continued

```
<210> SEQ ID NO 18
<211> LENGTH: 354
<212> TYPE: DNA
<213> ORGANISM: Artificial Sequence
<220> FEATURE:
<223> OTHER INFORMATION: D11_VH_NT

<400> SEQUENCE: 18
gaagtgcagc tgctggaaag tggaggtgga ctggtgcagc ctggcggcag cctgcgcctg      60
agctgtgccg ccagcggatt caccttcagc gattattatt ggacctgggt tcgccaagca     120
cctggcaaag gcctggaatg ggtgagcggc tcacctgtgt ttggcgccgc taactatgcc     180
cagaactttc agggccgctt taccatcagc cgcgataaca gcaaaaacac cctgtatctg     240
cagatgaaca gcctgcgcgc cgaggacacc gcagtctact actgtgccaa agccggcttt     300
accggcggcc attttgatat ctggggacaa ggtactctgg tgaccgtgag cagc           354

<210> SEQ ID NO 19
<211> LENGTH: 324
<212> TYPE: DNA
<213> ORGANISM: Artificial Sequence
<220> FEATURE:
<223> OTHER INFORMATION: D11_VL_NT

<400> SEQUENCE: 19
cagagcgtgc tgacccagcc tcctagcgcc tccggtacac caggacagcg cgtgactatt      60
agctgtagcg gcagcagcag caacatcggc aacaactatg tgagctggta ccagcaactg     120
cctggaactg cacctaagct gctgatctat ggcaacagca accgccctag cggcgtgcct     180
aatcgcttta gcggtagcaa atcaggcacc agcgccagcc tggccatcag cggtcttcgc     240
tccgaagatg aagccgatta ttattgtcag agctatgata gcagcagctg gctgtttggt     300
ggcggtacca agctgaccgt gctg                                            324

<210> SEQ ID NO 20
<211> LENGTH: 1344
<212> TYPE: DNA
<213> ORGANISM: Artificial Sequence
<220> FEATURE:
<223> OTHER INFORMATION: D11_IGG-H_NT

<400> SEQUENCE: 20
gaagtgcagc tgctggaaag tggaggtgga ctggtgcagc ctggcggcag cctgcgcctg      60
agctgtgccg ccagcggatt caccttcagc gattattatt ggacctgggt tcgccaagca     120
cctggcaaag gcctggaatg ggtgagcggc tcacctgtgt ttggcgccgc taactatgcc     180
cagaactttc agggccgctt taccatcagc cgcgataaca gcaaaaacac cctgtatctg     240
cagatgaaca gcctgcgcgc cgaggacacc gcagtctact actgtgccaa agccggcttt     300
accggcggcc attttgatat ctggggacaa ggtactctgg tgaccgtgag cagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca gaaagttga gcccaaatct     660 tgcgacaaaa ctcacacatg cccaccgtgc ccagcacctg aactcctggg gggaccgtca     720
gtcttcctct tccccccaaa acccaaggac accctcatga tctcccggac ccctgaggtc     780
```

```
acatgcgtgg tggtggacgt gagccacgaa gaccctgagg tcaagttcaa ctggtacgtg      840
gacggcgtgg aggtgcataa tgccaagaca aagccgcggg aggagcagta caacagcacg      900
taccgtgtgg tcagcgtcct caccgtcctg caccaggact ggctgaatgg caaggagtac      960
aagtgcaagg tctccaacaa agccctccca gcccccatcg agaaaaccat ctccaaagcc     1020
aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctacagcaag ctcaccgtgg acaagagcag gtggcagcag     1260
gggaacgtct tctcatgctc cgtgatgcat gaggctctgc acaaccacta cacgcagaag     1320
agcctctccc tgtccccggg taaa                                            1344

<210> SEQ ID NO 21
<211> LENGTH: 642
<212> TYPE: DNA
<213> ORGANISM: Artificial Sequence
<220> FEATURE:
<223> OTHER INFORMATION: D11_IGG-L_NT

<400> SEQUENCE: 21
cagagcgtgc tgacccagcc tcctagcgcc tccggtacac caggacagcg cgtgactatt       60
agctgtagcg gcagcagcag caacatcggc aacaactatg tgagctggta ccagcaactg      120
cctggaactg cacctaagct gctgatctat ggcaacagca accgccctag cggcgtgcct      180
aatcgcttta gcggtagcaa atcaggcacc agcgccagcc tggccatcag cggtcttcgc      240
tccgaagatg aagccgatta ttattgtcag agctatgata gcagcagctg ctgtttggt       300 ggcggtacca agctgaccgt gctgggtcag cccaaggctg ccccctcggt cacgctcttc      360
ccaccctcct ctgaggagct tcaagccaac aaggccacac tggtgtgtct cataagtgac      420
ttctacccgg agccgtgac agtggcctgg aaggcagata gcagcccgt caaggcggga      480 gtggagacca ccacaccctc caacaaagc aacaacaagt acgcggccag cagctacctg      540
agcctgacgc ctgagcagtg gaagtcccac aaaagctaca gctgccaggt cacgcatgaa      600
gggagcaccg tggagaagac agtggcccct gcagaatgct ct                       642

<210> SEQ ID NO 22
<211> LENGTH: 117
<212> TYPE: PRT
<213> ORGANISM: Artificial Sequence
<220> FEATURE:
<223> OTHER INFORMATION: D11-B9_VH_AA

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Trp Thr Trp Val Arg Gln Ala Pro Gly Lys Gly Leu Glu Trp Val
        35                  40                  45

Ser Gly Ser Pro Val Phe Gly Ala Ala Asn Tyr Ala Gln Asn Phe Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Lys Ala Gly Ile Pro Gly His Phe Asp Ile Trp Gly Gln Gly Thr Leu
            100                 105                 110

Val Thr Val Ser Ser
        115

<210> SEQ ID NO 23
<211> LENGTH: 108
<212> TYPE: PRT
<213> ORGANISM: Artificial Sequence
<220> FEATURE:
<223> OTHER INFORMATION: D11-B9_VL_AA

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly Asn Ser Asn Arg Pro Ser Gly Val Pro Asn Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Ser
                85                  90                  95

Trp Leu Phe Gly Gly Gly Thr Lys Leu Thr Val Leu
            100                 105

<210> SEQ ID NO 24
<211> LENGTH: 447
<212> TYPE: PRT
<213> ORGANISM: Artificial Sequence
<220> FEATURE:
<223> OTHER INFORMATION: D11-B9_IGG-H_AA

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Trp Thr Trp Val Arg Gln Ala Pro Gly Lys Gly Leu Glu Trp Val
        35                  40                  45

Ser Gly Ser Pro Val Phe Gly Ala Ala Asn Tyr Ala Gln Asn Phe Gln
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ala Gly Ile Pro Gly His Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

-continued

```
                165              170              175

Ser Gly Leu Tyr Ser Leu Ser Ser Val Val Thr Val Pro Ser Ser Ser
            180              185              190

Leu Gly Thr Gln Thr Tyr Ile Cys Asn Val Asn His Lys Pro Ser Asn
            195              200              205

Thr Lys Val Asp Lys Lys Val Glu Pro Lys Ser Cys Asp Lys Thr His
    210              215              220

Thr Cys Pro Pro Cys Pro Ala Pro Glu Leu Leu Gly Gly Pro Ser Val
225              230              235              240

Phe Leu Phe Pro Pro Lys Pro Lys Asp Thr Leu Met Ile Ser Arg Thr
            245              250              255

Pro Glu Val Thr Cys Val Val Val Asp Val Ser His Glu Asp Pro Glu
            260              265              270

Val Lys Phe Asn Trp Tyr Val Asp Gly Val Glu Val His Asn Ala Lys
            275              280              285

Thr Lys Pro Arg Glu Glu Gln Tyr Asn Ser Thr Tyr Arg Val Val Ser
    290              295              300

Val Leu Thr Val Leu His Gln Asp Trp Leu Asn Gly Lys Glu Tyr Lys
305              310              315              320

Cys Lys Val Ser Asn Lys Ala Leu Pro Ala Pro Ile Glu Lys Thr Ile
            325              330              335

Ser Lys Ala Lys Gly Gln Pro Arg Glu Pro Gln Val Tyr Thr Leu Pro
            340              345              350

Pro Ser Arg Asp Glu Leu Thr Lys Asn Gln Val Ser Leu Thr Cys Leu
            355              360              365

Val Lys Gly Phe Tyr Pro Ser Asp Ile Ala Val Glu Trp Glu Ser Asn
    370              375              380

Gly Gln Pro Glu Asn Asn Tyr Lys Thr Thr Pro Pro Val Leu Asp Ser
385              390              395              400

Asp Gly Ser Phe Phe Leu Tyr Ser Lys Leu Thr Val Asp Lys Ser Arg
            405              410              415

Trp Gln Gln Gly Asn Val Phe Ser Cys Ser Val Met His Glu Ala Leu
            420              425              430

His Asn His Tyr Thr Gln Lys Ser Leu Ser Leu Ser Pro Gly Lys
            435              440              445
```

<210> SEQ ID NO 25
<211> LENGTH: 214
<212> TYPE: PRT
<213> ORGANISM: Artificial Sequence
<220> FEATURE:
<223> OTHER INFORMATION: D11-B9_IGG-L_AA

<400> SEQUENCE: 25

```
Gln Ser Val Leu Thr Gln Pro Pro Ser Ala Ser Gly Thr Pro Gly Gln
1               5               10              15

Arg Val Thr Ile Ser Cys Ser Gly Ser Ser Ser Asn Ile Gly Asn Asn
            20              25              30

Tyr Val Ser Trp Tyr Gln Gln Leu Pro Gly Thr Ala Pro Lys Leu Leu
            35              40              45

Ile Tyr Gly Asn Ser Asn Arg Pro Ser Gly Val Pro Asn Arg Phe Ser
    50              55              60

Gly Ser Lys Ser Gly Thr Ser Ala Ser Leu Ala Ile Ser Gly Leu Arg
65              70              75              80

Ser Glu Asp Glu Ala Asp Tyr Tyr Cys Gln Ser Tyr Asp Ser Ser Ser
```

-continued

```
                85                90                95

Trp Leu Phe Gly Gly Gly Thr Lys Leu Thr Val Leu Gly Gln Pro Lys
            100                105                110

Ala Ala Pro Ser Val Thr Leu Phe Pro Pro Ser Ser Glu Glu Leu Gln
        115                120                125

Ala Asn Lys Ala Thr Leu Val Cys Leu Ile Ser Asp Phe Tyr Pro Gly
        130                135                140

Ala Val Thr Val Ala Trp Lys Ala Asp Ser Ser Pro Val Lys Ala Gly
145                150                155                160

Val Glu Thr Thr Thr Pro Ser Lys Gln Ser Asn Asn Lys Tyr Ala Ala
                165                170                175

Ser Ser Tyr Leu Ser Leu Thr Pro Glu Gln Trp Lys Ser His Lys Ser
            180                185                190

Tyr Ser Cys Gln Val Thr His Glu Gly Ser Thr Val Glu Lys Thr Val
            195                200                205

Ala Pro Ala Glu Cys Ser
    210

<210> SEQ ID NO 26
<211> LENGTH: 351
<212> TYPE: DNA
<213> ORGANISM: Artificial Sequence
<220> FEATURE:
<223> OTHER INFORMATION: D11-B9_VH_NT

<400> SEQUENCE: 26
gaagtgcagc tgctggaaag tggaggtgga ctggtgcagc ctggcggcag cctgcgcctg      60
agctgtgccg ccagcggatt caccttcagc gattattatt ggacctgggt tcgccaagca     120
cctggcaaag gctggaatg ggtgagcggc tcacctgtgt ttggcgccgc taactatgcc     180
cagaactttc agggccgctt taccatcagc cgcgataaca gcaaaaacac cctgtatctg     240
cagatgaaca gcctgcgcgc cgaggacacc gcagtctact actgtgccaa agccggtatt     300
cctggccatt ttgatatctg gggacaaggt actctggtga ccgtgagcag c             351

<210> SEQ ID NO 27
<211> LENGTH: 324
<212> TYPE: DNA
<213> ORGANISM: Artificial Sequence
<220> FEATURE:
<223> OTHER INFORMATION: D11-B9_VL_NT

<400> SEQUENCE: 27
cagagcgtgc tgacccagcc tcctagcgcc tccggtacac caggacagcg cgtgactatt      60
agctgtagcg gcagcagcag caacatcggc aacaactatg tgagctggta ccagcaactg     120
cctggaactg cacctaagct gctgatctat ggcaacagca ccgccctag cggcgtgcct     180 aatcgcttta gcggtagcaa atcaggcacc agcgccagcc tggccatcag cggtcttcgc     240
tccgaagatg aagccgatta ttattgtcag agctatgata gcagcagctg gctgtttggt     300
ggcggtacca agctgaccgt gctg                                           324

<210> SEQ ID NO 28
<211> LENGTH: 1341
<212> TYPE: DNA
<213> ORGANISM: Artificial Sequence
<220> FEATURE:
<223> OTHER INFORMATION: D11-B9_IGG-H_NT

<400> SEQUENCE: 28
```

```
gaagtgcagc tgctggaaag tggaggtgga ctggtgcagc ctggcggcag cctgcgcctg      60
agctgtgccg ccagcggatt caccttcagc gattattatt ggacctgggt tcgccaagca     120
cctggcaaag gcctggaatg ggtgagcggc tcacctgtgt ttggcgccgc taactatgcc     180
cagaactttc agggccgctt taccatcagc cgcgataaca gcaaaaacac cctgtatctg     240
cagatgaaca gcctgcgcgc cgaggacacc gcagtctact actgtgccaa agccggtatt     300
cctggccatt ttgatatctg gggacaaggt actctggtga ccgtgagcag cgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagccc caaatcttgc     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg     1260 aacgtcttct catgctccgt gatgcatgag gctctgcaca accactacac gcagaagagc    1320
ctctccctgt ccccgggtaa a                                              1341

<210> SEQ ID NO 29
<211> LENGTH: 642
<212> TYPE: DNA
<213> ORGANISM: Artificial Sequence
<220> FEATURE:
<223> OTHER INFORMATION: D11-B9_IGG-L_NT

<400> SEQUENCE: 29
cagagcgtgc tgacccagcc tcctagcgcc tccggtacac caggacagcg cgtgactatt      60
agctgtagcg gcagcagcag caacatcggc aacaactatg tgagctggta ccagcaactg     120
cctggaactg cacctaagct gctgatctat ggcaacagca accgccctag cggcgtgcct     180
aatcgcttta gcggtagcaa atcaggcacc agcgccagcc tggccatcag cggtcttcgc     240
tccgaagatg aagccgatta ttattgtcag agctatgata gcagcagctg gctgtttggt     300
ggcggtacca agctgaccgt gctgggtcag cccaaggctg cccctcggt cacgctcttc      360 ccaccctcct ctgaggagct tcaagccaac aaggccacac tggtgtgtct cataagtgac     420
ttctacccgg agccgtgac agtggcctgg aaggcagata gcagcccgt caaggcggga      480 gtggagacca ccacaccctc aaacaaagc aacaacagt acgcggccag cagctacctg      540
agcctgacgc ctgagcagtg gaagtcccac aaaagctaca gctgccaggt cacgcatgaa     600
gggagcaccg tggagaagac agtggcccct gcagaatgct ct                        642
```

ANTI-OSCAR ANTIBODY FOR PREVENTING OR TREATING OSTEOARTHRITIS

CROSS-REFERENCE TO RELATED APPLICATIONS

This application is a § 371 National Stage of International Application No. PCT/KR2020/007086 filed Jun. 1, 2020, which claims priority to KR Application No. 10-2019-0066154, filed Jun. 4, 2019, and KR Application No. 10-2020-0064933 filed May 29, 2020, the entire contents of which are hereby incorporated by reference.

INCORPORATION OF SEQUENCE LISTING

The sequence listing that is contained in the file named "HANO-P0045US_Corrected_Sequence_Listing", which is 45 KB (as measured in Microsoft Windows®) and was created on Aug. 21, 2023, is filed herewith by electronic submission and is incorporated by reference herein.

TECHNICAL FIELD

The present invention relates to a composition for preventing or treating osteoarthritis, including an osteoclast-associated Ig-like receptor (OSCAR) protein inhibitor, a polynucleotide encoding an anti-OSCAR antibody or a fragment thereof, and an OSCAR protein inhibitor screening method.

BACKGROUND ART

Osteoarthritis (OA) accompanied by local inflammation and pain resulting from damage or degeneration of articular cartilage is a major disease lowering the quality of life and limiting normal social activities of the elderly. In general, osteoarthritis is more prevalent among women than among men, and 30% of the population over 60 years old have osteoarthritis. The number of patients tends to significantly increase as the aged population increases. According to an LEK report, it is estimated that the incidence of osteoarthritis in the United States will increase by 2.8% every year from 2014 to 2028. Recently, incidence of osteoarthritis among younger people has also tended to increase due to traumatic stress or high heels, etc in the case of young women.

There is no accurate therapeutic agent in existing treatment for osteoarthritis, and non-pharmacological treatment has been performed more than pharmacological treatment. NSAID-based analgesic and anti-inflammatory drugs, steroidal drugs, glucosamine, and the like, which relieve symptoms, e.g., inflammation and pain, may be used as drugs for treatment, and a method of using hyaluronic acid that protects joints via lubrication action by intra-articular injection has been mainly used.

In cases where the symptoms of osteoarthritis are severe, non-pharmacological treatment such as artificial joint replacement surgery is carried out. However, due to the need for rehabilitation, limited life-span of artificial joints (within 10 years), high costs, and side effects such as inflammation caused by corroded artificial joints and secondary inflammation, it is necessary to delay a possible surgery as long as possible from a clinical point of view. Considering the efficacy and side effects of existing treatment, there is a need to develop a novel safe therapeutic agent which is effective in preventing joints from wearing away.

Osteoclast-associated Ig-like receptor (OSCAR), as a member of the leukocyte receptor complex family, is a cell surface receptor including two immunoglobulin (Ig) domains. When OSCAR was first discovered, a function of regulating differentiation of osteoclasts via osteoclast-specific expression was reported (*J Exp Med.* 2002, 21; 195(2): 201-9). Although OSCAR includes two Ig domains that recognize a ligand, it lacks a cytoplasmic tail domain that mediates intracellular signaling. Such receptor mediates signaling by binding to another receptor including an immunoreceptor tyrosine-based activation motif (ITAM). As a receptor binding to OSCAR to mediate intracellular signaling, FcRγ was confirmed.

Differentiation of osteoclasts is regulated by interaction between osteoclasts and osteoblasts. It has been reported that during this process, the osteoblasts secrete collagen to the outside of the cells, and the secreted collagen serves as a ligand of OSCAR. In recent years, the molecular mechanism in which OSCAR recognizes collagen and binds thereto has been interpreted by a structure obtained by X-ray diffraction analysis. In addition, the possibility that the OSCAR protein contributes to rheumatoid arthritis has been reported based on a result wherein secretion of inflammatory cytokines is promoted in monocytes by binding between OSCAR and collagen.

To date, no disease directly induced by the OSCAR protein has been reported. Also, no method of inhibiting binding between OSCAR and collagen has been reported, nor any system for searching for substances inhibiting binding between the OSCAR protein and collagen. Substances having the activity to inhibit binding between collagen and OSCAR (an antibody, low-molecular-weight compound, or the like) are expected to inhibit the function (activity) of OSCAR. Therefore, such substances may be used as inhibitors for diseases induced by the collagen-OSCAR binding.

DISCLOSURE

Technical Problem

The present invention relates to a composition for preventing or treating osteoarthritis, including an osteoclast-associated Ig-like receptor (OSCAR) protein inhibitor, a polynucleotide encoding an anti-OSCAR antibody or a fragment thereof, and an OSCAR protein inhibitor screening method.

However, the technical problems to be solved by the present invention are not limited to the aforementioned problems, and any other technical problems not mentioned herein will be clearly understood from the following description by those skilled in the art to which the present invention pertains.

Technical Solution

A first aspect of the present invention provides a composition for preventing or treating osteoarthritis including an osteoclast-associated Ig-like receptor (OSCAR) protein inhibitor.

A second aspect of the present invention provides an isolated antibody binding to OSCAR protein or a fragment thereof.

A third aspect of the present invention provides a polynucleotide encoding the isolated antibody or a fragment thereof.

A fourth aspect of the present invention provides an expression vector including the polynucleotide encoding the isolated antibody or a fragment thereof.

A fifth aspect of the present invention provides a transformant other than a human including the expression vector.

A sixth aspect of the present invention provides a method of preparing an anti-OSCAR antibody or a fragment thereof, the method including culturing the transformant.

A seventh aspect of the present invention provides a method of screening an OSCAR protein inhibitor, the method comprising: (a) culturing isolated chondrocytes and treating the cultured chondrocytes with a candidate substance for the OSCAR protein inhibitor; (b) treating the cultured chondrocytes with collagen; and (c) measuring an expression level of an osteoarthritis marker in the chondrocytes.

An eighth aspect of the present invention provides a method of preventing or treating osteoarthritis, the method including administering the composition for preventing or treating osteoarthritis of the present invention to a subject.

A ninth aspect of the present invention provides a composition for preventing or treating bone-related disease, including the isolated antibody or a fragment thereof, wherein the bone-related disease is osteoporosis or osteopenia.

Advantageous Effects

According to embodiments of the present invention, osteoarthritis may be prevented or treated by way of the mechanism of the anti-osteoclast-associated Ig-like receptor (OSCAR) antibody or a fragment thereof for inhibiting OSCAR-collagen interaction in chondrocytes, and the OSCAR protein inhibitor having excellent inhibitory effects on OSCAR-collagen interaction may be screened using the OSCAR protein inhibitor screening method of the present invention.

BRIEF DESCRIPTION OF DRAWINGS

FIGS. 3A-C show selection and an antagonistic effect of anti-OSCAR antibodies evaluated by a method of screening novel anti-OSCAR antibodies using mouse-derived chondrocytes.

FIGS. 4A-C show selection and an antagonistic effect of anti-OSCAR antibodies evaluated by method of screening novel anti-OSCAR antibodies using human-derived chondrocytes.

FIG. 7A shows a process of randomizing CDR-H3 of clone D11 and constructing focused libraries, and FIG. 7B shows panning results of D11-H3-1-6 libraries.

FIGS. 9A-B show results of serial dilution ELISA and 4-parameter logistic curve fit of seven types of clones obtained from an affinity maturation process of D11.

FIG. 10 shows Octet analysis results of antibody D11 and antibody D11-69 having improved affinity.

FIGS. 11A-B show results of histological analysis (FIG. 11A) and quantitative analysis (FIG. 11B) of efficacy of antibody D11 and antibody D11-B9 in an osteoarthritis animal model.

FIGS. 12A-C show results of histological analysis (FIG. 12A), quantitative analysis (FIG. 12B), and quantitative analysis of HC/CC distribution (FIG. 12C) thickness of subchondral plate in an osteoarthritis animal model by treatment with antibody D11 and antibody D11-69.

FIGS. 13A-C show results of histological analysis (FIG. 13A) and quantitative analysis (FIGS. 13B and 13C) of inhibitory effects on OSCAR protein signaling in an osteoarthritis animal model by treatment with antibody D11 and antibody D11-69.

FIGS. 14A-B show results of histological analysis (FIG. 14A) and quantitative analysis (FIG. 14B) of inhibitory effects on apoptosis of chondrocytes in an osteoarthritis animal model by treatment with antibody D11 and antibody D11-69.

BEST MODE

Figures 1, 2:
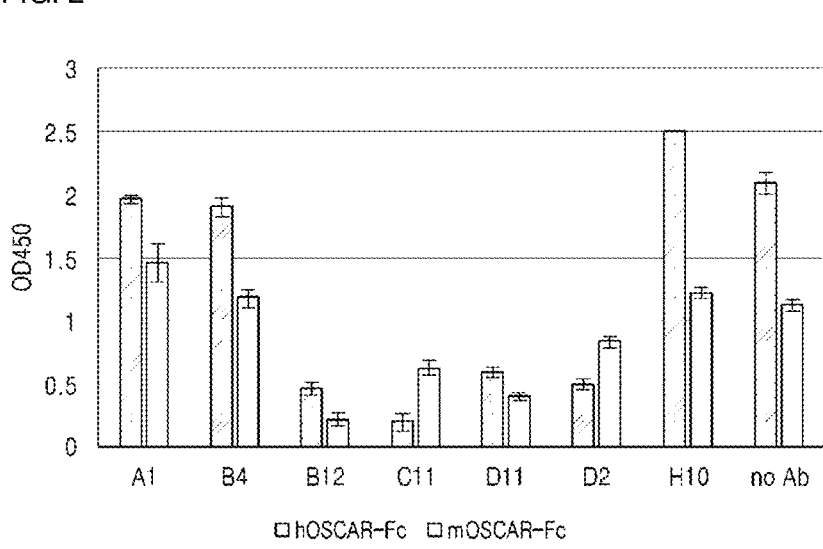
FIG. 1 shows binding affinity of seven novel scFvs discovered from antibody library panning to human and mouse OSCAR identified by ELISA.
FIG. 2 shows inhibitory effects of hIgG1 antibodies converted from the seven novel scFvs discovered from antibody library panning on OSCAR-collagen interaction identified by competitive ELISA.

As used herein, the "osteoclast-associated Ig-like receptor (OSCAR) protein", which is a member of the leukocyte receptor complex family, is a cell surface receptor including two immunoglobulin (Ig) domains. The OSCAR protein may bind to collagen, and it is known that a disease may be induced by the binding. In an embodiment of the present invention, OSCAR protein or a fragment thereof may be derived from humans or mice. Genetic information such as amino acid sequences of the OSCAR protein derived from humans and mice, and nucleotide sequences encoding the same may be available from known database such as GenBank of the National Center for Biotechnology Information (NCBI), without being limited thereto.

As used herein, the term "OSCAR protein-collagen interaction inhibitor" refers to any substance having an effect on inhibiting interaction or binding between OSCAR protein and collagen, specifically a substance binding to a collagen recognition site of the OSCAR protein to inhibit binding between the OSCAR protein and collagen, but is not limited thereto.

As used herein, the "collagen", as a protein, is a main component of connective tissue. Although mostly found in bones and skin, collagen is a component distributed throughout the whole body such as joints, membranes of organs, and hair. A total of 28 types of collagen are known, and the type of collagen is not limited as long as the collagen may bind to the OSCAR protein.

As used herein, the term "antibody" refers to an immunoglobulin selected from the group consisting of IgA, IgE, IgM, IgD, IgY, IgNAR, heavy chain antibody, and IgG, specifically one binding to a target antigen. The antibody consists of two light chains and two heavy chains, and each chain includes a variable domain having a variable amino acid sequence and a constant domain having a constant amino acid sequence. The antibody has an antigen binding site located at one end of a three-dimensional structure of the variable domains and formed of complementarity-determining regions, wherein three complementarity-determining regions are present in each of the light chain and the heavy chain. The complementarity-determining region is a region having particularly high amino acid sequence variability in the variable domains, and antibodies specific to various antigens may be discovered due to the high variability. Not only a full-length antibody but also antigen-binding fragments of the antibody molecule may also be included within the scope of the present invention.

As used herein, the term "antibody fragment" refers to any part of an antibody, for example, a scFv, a dsFv, Fab, Fab', F(ab')$_2$, a sdAb, a nanobody, or any combination thereof and may include an antigen recognition site, but is not limited thereto. The Fab, which has a structure including the variable domains of the light chain and the heavy chain, the constant domain of the light chain, and a first constant domain (CH1 domain) of the heavy chain, includes one antigen binding site. The Fab' is different from the Fab in that the Fab' has a hinge region including at least one cysteine residue at the C-terminus of the CH1 domain of the heavy chain. The F(ab')$_2$ antibody is generated by a disulfide bond of the cysteine residue of the hinge region of the Fab'. The variable fragment (Fv) refers to a minimal fragment of an antibody including only the heavy chain variable domain and the light chain variable domain. The disulfide-stabilized Fv (dsFv) refers to a fragment in which the heavy chain variable domain is linked to the light chain variable domain via a disulfide bond, and the single-chain Fv (scFv) generally refers to a fragment in which the heavy chain variable domain is linked to the light chain variable domain by a covalent bond via a peptide linker. These antibody fragments may be obtained by using protease (e.g., the Fab fragment may be obtained by cleaving the whole antibody with papain and the F(ab')$_2$ fragment may be obtained by cleaving the antibody with pepsin), preferably via genetic recombination technology. In addition, the sdAb and the nanobody are antibody fragments consisting of a single variable domain and may include, for example, an antibody fragment obtained from a naturally occurring heavy chain antibody comprising a single variable domain (VH) and two constant domains (CH2 and CH3) via proteolysis or genetic recombination of the variable domain, and a single-domain antibody fragment prepared by artificially modifying a variable domain of the light chain or the heavy chain, without being limited thereto.

As used herein, the term "antigen recognition site" refers to any fragment of the antibody of the present invention having antigen binding activity of the antibody and may be used interchangeably with "antigen-binding fragment" and "binding fragment of a peptide".

As used herein, the term "antibody Fc region" refers to a region consisting of the heavy chain constant domain 2 (CH$_2$) and the heavy chain constant domain 3 (CH$_3$) of an immunoglobulin excluding the variable domains of the heavy chain and the light chain, the heavy chain constant domain 1 (CH$_1$), and the light chain constant domain (CL$_1$) and may include a hinge region at the heavy chain constant domain. Since the antibody Fc region is a biodegradable polypeptide that is metabolized in vivo, it is safe for use as a drug carrier. Also, since the immunoglobulin Fc region has a relatively low molecular weight compared to the entire immunoglobulin molecule, it is beneficial in terms of preparation, purification, and yield of a conjugate. In addition, by removing the Fab region, which shows high non-homogeneity due to the difference in amino acid sequence between antibodies, effects on considerably increasing homogeneity and reducing the potential to induce serum antigenicity may be expected. The Fc region of the antibody may be an Fc region derived from IgG, IgA, IgD, IgE, IgM, or any combination or hybrid thereof, without being limited thereto.

Throughout the specification, the term "include" does not preclude the other elements but further adds another element, unless otherwise stated. The terms "about", "substantially", etc. used throughout the specification mean that when unique manufacturing and allowable error of substances are suggested, such an allowable error corresponds the value or is similar to the value, and such terms are intended for the sake of clear understanding of the present invention or to prevent an unconscious infringer from illegally using the disclosure of the present invention.

Throughout the specification, the term "any combination(s) thereof" recited in the expressions of Markush type means that at least one or more mixing or combination may be selected from a group consisting of multiple components recited in the expressions of the Markush type, and more specifically, it means that one or more components selected from a group consisting of components may be included.

Throughout the specification, the term "A and/or B" means "A or B, or A and B".

Hereinafter, embodiments and examples of the present invention will be described in detail with reference to the accompanying drawings. However, the present invention is not limited to these embodiments, examples, and drawings.

A first aspect of the present invention provides a composition for preventing or treating osteoarthritis, including an osteoclast-associated Ig-like receptor (OSCAR) protein inhibitor.

In an embodiment, the OSCAR protein inhibitor, as a substance that inhibits or suppresses expression level or activity of OSCAR protein, may inactivate an active site or binding site of the OSCAR protein, and specifically, it may inhibit or suppress binding and interaction between the OSCAR protein and collagen by inactivating a collagen binding site of the OSCAR protein.

In an embodiment of the present invention, the OSCAR protein inhibitor may be a substance inhibiting OSCAR protein-collagen interaction.

In an embodiment of the present invention, the composition for preventing or treating osteoarthritis may include an OSCAR protein-collagen interaction inhibitor.

In an embodiment of the present invention, the OSCAR protein-collagen interaction inhibitor may be anti-OSCAR antibodies, anti-OSCAR antibody fragments, proteins, oligopeptides, small organic molecules, polysaccharides, polynucleotides, compounds or any combination thereof capable of inhibiting binding between the OSCAR protein and collagen, and the inhibitor may include not only natural substances but also synthetic substances, without being limited thereto.

In an embodiment of the present invention, the OSCAR protein-collagen interaction inhibitor may be an anti-OSCAR antibody or a fragment thereof.

The anti-OSCAR antibody or a fragment thereof according to an embodiment of the present invention may be one binding to a region of the OSCAR protein, specifically one binding to a collagen binding site of the OSCAR protein to inhibit linkage between the OSCAR protein and collagen, without being limited thereto.

In an embodiment of the present invention, the OSCAR protein inhibitor may include an anti-OSCAR antibody or a fragment thereof.

In an embodiment of the present invention, the OSCAR protein inhibitor may be one inhibiting the activity of the OSCAR protein expressed in chondrocytes.

In an embodiment of the present invention, the anti-OSCAR antibody or a fragment thereof that include a heavy chain variable domain and a light chain variable domain may include at least one selected from the group consisting of: 1) an anti-OSCAR antibody or a fragment thereof including a heavy chain variable domain consisting of SEQ ID NO: 6 and a light chain variable domain consisting of SEQ ID NO: 7; 2) an anti-OSCAR antibody or a fragment thereof including a heavy chain variable domain consisting of SEQ ID NO: 14 and a light chain variable domain consisting of SEQ ID NO: 15; and 3) an anti-OSCAR antibody or a fragment thereof including a heavy chain variable domain consisting of SEQ ID NO: 22 and a light chain variable domain consisting of SEQ ID NO: 23.

Figure 5:
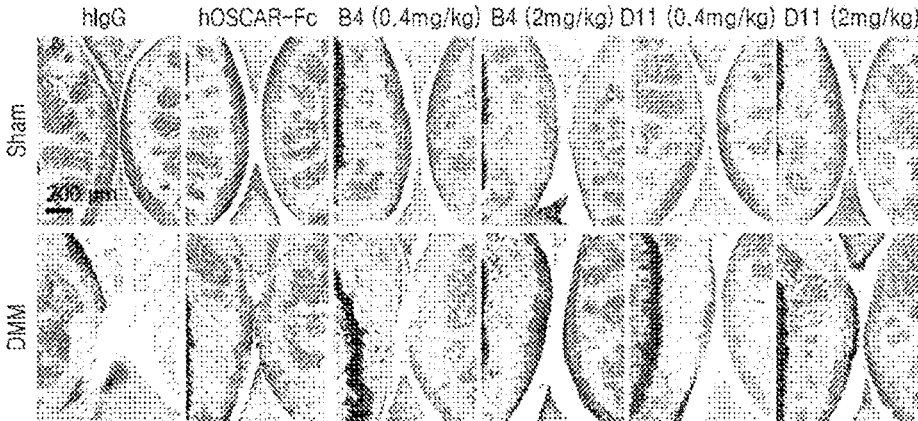
FIG. 5 shows histological efficacy analysis results of anti-OSCAR antibodies in an osteoarthritis model.

In an embodiment of the present invention, an anti-OSCAR antibody B4 includes the heavy chain variable domain consisting of SEQ ID NO: 6 and the light chain variable domain consisting of SEQ ID NO: 7, and an anti-OSCAR antibody D11 includes the heavy chain variable domain consisting of SEQ ID NO: 14 and the light chain variable domain consisting of SEQ ID NO: 15. It was confirmed that these antibodies bind to the OSCAR protein of humans and mice to inhibit interaction between the OSCAR protein and collagen (FIG. 2). In addition, in the case of treatment with these antibodies, it was confirmed that the expression level of an osteoarthritis marker decreased (FIG. 4) and symptoms were relieved in an osteoarthritis animal model (FIG. 5), and thus it can be seen that the anti-OSCAR antibodies B4 and D11 according to the present invention may be available as therapeutic agents for osteoarthritis.

Also, it was confirmed that an antibody D11-B9 prepared by modifying the anti-OSCAR antibody D11 by replacing phenylalanine-threonine-glycine (FTG) of the heavy chain variable domain with isoleucine-proline (IP) (substituting phenylalanine-threonine-glycine, which are the $100^{th}$, $101^{st}$, and $102^{nd}$ amino acids of the amino acid sequence of SEQ ID NO: 6, with isoleucine-proline), had superior effects to those of the antibody D11 (FIGS. 10 to 14). The anti-OSCAR antibody D11-B9 includes a heavy chain variable domain consisting of SEQ ID NO: 22 and a light chain variable domain consisting of SEQ ID NO: 23.

In an embodiment of the present invention, the anti-OSCAR antibody may be an IgG antibody and may include at least one selected from the group consisting of: 1) an antibody (B4) including a heavy chain consisting of SEQ ID NO: 8 and a light chain consisting of SEQ ID NO: 9; 2) an antibody (D11) including a heavy chain consisting of SEQ ID NO: 16 and a light chain consisting of SEQ ID NO: 17; and 3) an antibody (D11-B9) including a heavy chain consisting of SEQ ID NO: 24 and a light chain consisting of SEQ ID NO: 25.

Peptides according to an embodiment of the present invention may include not only peptides including the above-described SEQ ID NOS, but also peptides having a homology of 80% or more, 85% or more, 90% or more, 91% or more, 92% or more, 93% or more, 94% or more, 95% or more, 96% or more, 97% or more, 98% or more, or 99% or more to the amino acid sequence as long as each peptide has biological activity identical or equivalent to that of the peptides.

It will be obvious that any peptides having the amino acid sequence including deletion, modification, substitution, or addition of one or several amino acids is within the scope of the present invention as long as the amino acid sequence retains the above-described homology and biological activity substantially identical or equivalent to that of the above-described peptides.

As used herein, the term "homology" refers to relatedness between two amino acid sequences or polynucleotide sequences and may be expressed as a percentage. In the present invention, a homologous sequence having activity identical or similar to that of the provided amino acid sequence or nucleotide sequence is expressed through "% homology". For example, the % homology may be confirmed using standard software for calculating parameters such as score, identity, and similarity, specifically BLAST2.0, or by comparing sequences via hybridization experiments under defined strict conditions, and the defined strict hybridization conditions may be determined by way of a method known to a skilled person in the art [e.g., J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York]. As used herein, the term "stringent conditions" refers to conditions which permit specific hybridization between polynucleotides. Such conditions are disclosed in detail in known documents [e.g., J. Sambrook et al., supra].

As used herein, the term "degenerative arthritis" is a disease accompanied by inflammation and pain resulting from damage to bones and ligaments constituting a joint caused by damage or degenerative changes in cartilage that covers and protects the joint, and the degenerative arthritis is also referred to as osteoarthritis. Although a cause of primary (idiopathic) osteoarthritis is not clearly revealed, it is considered to be affected by gender, genetic factors, obesity, particular areas of joints, or the like, and a cause of secondary osteoarthritis may be trauma, disease, and deformity that may damage joint cartilage. The most common symptom in the early stages is pain in a local area around a joint where arthritis occurs, and one of the differences from rheumatoid arthritis is the lack of systematic symptoms. Since osteoarthritis is caused by degenerative changes in articular cartilage, no method of completely stopping these changes has been reported. Treatment of osteoarthritis aims to provide mental stability by helping a patient to understand the nature of the disease, while relieving pain, maintaining the function of the joint, and preventing deformation of the joint. However, when the joint is deformed already, the treatment aims to prevent the progression of damage to the joint by a surgery and rehabilitation and help the patient in daily life by increasing the range of motion without causing pain.

As used herein, the term "treatment" refers to all actions that ameliorate or beneficially change symptoms of osteoarthritis via administration of the composition of the present invention.

As used herein, the term "prevention" refers to all actions that inhibit or delay the onset of osteoarthritis or the possibility of the onset of osteoarthritis via administration of the composition of the present invention.

According to an embodiment of the present invention, the composition may further include a pharmaceutically acceptable carrier. For oral administration, a binder, a lubricant, a disintegrant, an excipient, a solubilizer, a dispersant, a stabilizer, a suspending agent, a coloring agent, a flavoring agent, and the like may be used. For injectable preparations, a buffering agent, a preservative, an analgesic, a solubilizer, an isotonic agent, a stabilizer, and the like may be used in a mixed form. For topical administration, a base, an excipient, a lubricant, a preservative, and the like may be used. The pharmaceutical composition of the present invention may be formulated into various dosage forms in combination with the above-mentioned pharmaceutically acceptable carriers. For example, for oral administration, the pharmaceutical composition may be formulated into tablets, troches, capsules, elixirs, suspensions, syrups, wafers, and the like. For injectable preparations, the pharmaceutical composition may be formulated into a single-dose ampoule or multidose form. The pharmaceutical composition may typically include a surfactant facilitating migration across a membrane. The surfactant may be a surfactant derived from a steroid, a cationic lipid such as N-[1-(2,3-dioleoyl)propyl-N,N,N-trimethylammoniumchloride (DOTMA), or various compounds such as cholesterol hemisuccinate and phosphatidyl glycerol.

A second aspect of the present invention provides an isolated antibody binding to OSCAR protein or a fragment thereof. The descriptions of the present invention provided above with reference to the first aspect also apply to the isolated antibody and a fragment thereof according to the second aspect of the present invention.

In an embodiment of the present invention, the isolated antibody or a fragment thereof that include a heavy chain variable domain and a light chain variable domain may include at least one selected from the group consisting of: 1) an isolated antibody or a fragment thereof (B4) including a heavy chain variable domain consisting of SEQ ID NO: 6 and a light chain variable domain consisting of SEQ ID NO: 7; 2) an isolated antibody or a fragment thereof (D11) including a heavy chain variable domain consisting of SEQ ID NO: 14 and a light chain variable domain consisting of SEQ ID NO: 15; and 3) an isolated antibody or a fragment thereof (D11-B9) including a heavy chain variable domain consisting of SEQ ID NO: 22 and a light chain variable domain consisting of SEQ ID NO: 23.

In an embodiment of the present invention, the heavy chain variable domain consisting of SEQ ID NO: 22 may be one prepared by substituting phenylalanine-threonine-glycine, which are the $100^{th}$, $101^{st}$, and $102^{nd}$ amino acids of a heavy chain variable domain consisting of SEQ ID NO: 14, with isoleucine-proline.

In an embodiment of the present invention, the anti-OSCAR antibody may be IgG antibody and may include at least one selected from the group consisting of: 1) an antibody including a heavy chain consisting of SEQ ID NO: 8 and a light chain consisting of SEQ ID NO: 9; 2) an antibody including a heavy chain consisting of SEQ ID NO: 16 and a light chain consisting of SEQ ID NO: 17; and 3) an antibody including a heavy chain consisting of SEQ ID NO: 24 and a light chain consisting of SEQ ID NO: 25.

In an embodiment of the present invention, the heavy chain variable domain consisting of SEQ ID NO: 24 may be one prepared by substituting phenylalanine-threonine-glycine, which are the $100^{th}$, $101^{st}$, and $102^{nd}$ amino acids of a heavy chain variable domain consisting of SEQ ID NO: 16, with isoleucine-proline.

In an embodiment of the present invention, the isolated antibody or a fragment thereof bind to the OSCAR protein or a fragment thereof to inhibit binding between the OSCAR protein and collagen, thereby inhibiting OSCAR protein-collagen interaction, signaling thereby, and effects thereof, and specifically, the isolated antibody or a fragment thereof may bind to a collagen recognition site or collagen binding site of the OSCAR protein or a fragment thereof.

In an embodiment of the present invention, the isolated antibody or a fragment thereof may be used in a composition for preventing or treating bone-related diseases including osteoarthritis.

A third aspect of the present invention provides a polynucleotide encoding an anti-OSCAR antibody or a fragment thereof. The descriptions of the present invention provided above in the first and second aspects also apply to the polynucleotide according to the third aspect of the present invention.

As used herein, the term "polynucleotide" refers to DNA encoding genetic information as a polymer of nucleotides.

According to an embodiment of the present invention, the polynucleotide may include a nucleotide sequence encoding at least one selected from the group consisting of: 1) an isolated antibody or a fragment thereof including a heavy chain variable domain consisting of SEQ ID NO: 6 and a light chain variable domain consisting of SEQ ID NO: 7; 2) an isolated antibody or a fragment thereof including a heavy chain variable domain consisting of SEQ ID NO: 14 and a light chain variable domain consisting of SEQ ID NO: 15; and 3) an isolated antibody or a fragment thereof including a heavy chain variable domain consisting of SEQ ID NO: 22 and a light chain variable domain consisting of SEQ ID NO: 23.

According to an embodiment of the present invention, the polynucleotide may include at least one selected from the group consisting of: 1) a polynucleotide encoding an isolated antibody including SEQ ID NO: 10 and SEQ ID NO: 11 or a fragment thereof; 2) a polynucleotide encoding an isolated antibody including SEQ ID NO: 18 and SEQ ID NO: 19 or a fragment thereof; and 3) a polynucleotide encoding an isolated antibody including SEQ ID NO: 26 and SEQ ID NO: 27 or a fragment thereof.

According to an embodiment of the present invention, the polynucleotide may include a nucleotide sequence encoding at least one selected from the group consisting of: 1) an isolated antibody including a heavy chain consisting of SEQ ID NO: 8 and a light chain consisting of SEQ ID NO: 9 or a fragment thereof; 2) an isolated antibody including a heavy chain consisting of SEQ ID NO: 16 and a light chain consisting of SEQ ID NO: 17 or a fragment thereof; and 3) an isolated antibody including a heavy chain consisting of SEQ ID NO: 24 and a light chain consisting of SEQ ID NO: 25 or a fragment thereof.

According to an embodiment of the present invention, the polynucleotide may include at least one selected from the group consisting of: 1) a polynucleotide encoding an isolated antibody or a fragment thereof including SEQ ID NO: 12 and SEQ ID NO: 13; 2) a polynucleotide encoding an isolated antibody or a fragment thereof including SEQ ID NO: 20 and SEQ ID NO: 21; and 3) a polynucleotide encoding an isolated antibody or a fragment thereof including SEQ ID NO: 28 and SEQ ID NO: 29.

In an embodiment of the present invention, the nucleotide sequences encoding the isolated antibodies or fragments thereof may include not only the nucleotide sequences encoding the amino acids as set forth in each SEQ ID NO, but also nucleotide sequences encoding a protein having homology of 80% or more, specifically 90% or more, more specifically 95% or more, even more specifically 98% or more, and most specifically 99% or more to the nucleotide sequences as long as the protein has effects substantially identical or equivalent to those of the proteins. Also, it will be obvious that any amino acid sequence including deletion, modification, substitution, or addition of one or several amino acids is within the scope of the present invention as long as the amino acid sequence retains the above-described homology and biological activity substantially identical or equivalent to that of the protein substantially set forth in the SEQ ID NO.

In an embodiment of the present invention, the nucleotide sequences encoding the isolated antibody or a fragment thereof may include a polynucleotide encoding a protein including the above-described amino acid sequence of the SEQ ID NO or an amino acid sequence having a homology of 80% or more, 85% or more, 90% or more, 91% or more, 92% or more, 93% or more, 94% or more, 95% or more, 96% or more, 97% or more, 98% or more, or 99% or more to the disclosed SEQ ID NO as long as the protein retains biological activity identical or equivalent thereto. In addition, the polynucleotide encoding the proteins may include various modifications made in a coding region provided not to change the amino acid sequence of the protein expressed from the coding region by codon degeneracy or in consideration of codons preferred by a living organism in which the protein is expressed. Therefore, any nucleotide sequence encoding each protein may be included in the polynucleotide without limitation. In addition, the polynucleotide may include any probe prepared from any known gene sequences, e.g., a nucleotide sequence hybridized with a sequence totally or partially complementary to the above-described nucleotide sequence under stringent conditions to encode a protein having the activity of the isolated antibody and a fragment thereof, without limitation.

As used herein, the term "stringent conditions" refers to conditions allowing specific hybridization between poly-nucleotides. Such conditions are disclosed in detail in known documents (e.g., Sambrook et al., supra, 9.50-9.51, 11.7-11.8). For example, the stringent conditions may include performing hybridization between polynucleotides having a high homology, e.g., a homology of 40% or more, specifically 90% or more, more specifically 95% or more, even more specifically 97% or more, or most specifically 99% or more homology, without performing hybridization between polynucleotides having a homology lower than the above homologies, or washing once, specifically twice or three times, under conventional washing conditions for Southern hybridization at a salt concentration and tempera-ture of 60° C., 1×SSC, 0.1% SDS, specifically 60° C., 0.1×SSC, 0.1% SDS, and more specifically 68° C., 0.1× SSC, 0.1% SDS.

Hybridization requires that two polynucleotides have complementary sequences, although bases may mismatch according to the degree of stringency of hybridization. The term "complementary" is used to describe the relationship between bases of nucleotides capable of hybridizing with each other. For example, with respect to DNA, adenine is complementary to thymine, and cytosine is complementary to guanine. Thus, the present invention may include not only substantially similar nucleotide sequences of the polynucle-otides but also polynucleotide fragments which are isolated but complementary to the entire sequence.

Specifically, polynucleotides having a homology may be detected using hybridization conditions including a hybrid-ization process at a $T_m$ value of 55° C. and the above-described conditions. Also, the $T_m$ value may be, but is not limited to, 63° C., or 65° C., and may be appropriately adjusted by those skilled in the art according to the intended purposes. An appropriate degree of stringency for hybrid-ization of the polynucleotides may depend on lengths and a degree of complementarity of the polynucleotides, and parameters thereof are well known in the art (Sambrook et al., supra, 9.50-9.51, 11.7-11.8).

A fourth aspect of the present invention provides an expression vector including the polynucleotide according to the third aspect of the present invention. The descriptions of the present invention provided above in the first to third aspects also apply to the expression vector according to the fourth aspect of the present invention.

As used herein, the "expression vector", as a recombinant vector capable of expressing a target protein in a proper host cell, is a gene construct including an essential regulatory element operably linked to express a gene insert.

As used herein, the term "operably linked" means that a nucleic acid sequence encoding a desired protein is func-tionally linked to a nucleic acid expression regulatory sequence to perform general functions. The operable linkage with a recombinant vector may be obtained by way of a genetic recombination technique well known in the art, and site-specific DNA cleavage and ligation may be performed using an enzyme well known in the art.

A proper expression vector of the present invention may include a signal sequence for membrane targeting or secre-tion in addition to expression regulatory elements such as a promoter, a start codon, a stop codon, a polyadenylation signal, and an enhancer. The start codon and stop codon, generally considered as a part of a nucleotide sequence encoding an immunogenic target protein, should exhibit action in a subject when a gene construct is introduced and should be present in-frame with a coding sequence. A common promoter may be constitutive or inducible. In the case of prokaryotic cells, lac, tac, T3, and T7 promoters may be used, and in the case of eukaryotic cells, not only a simian virus 40 (SV40), a mouse mammary tumor virus (MMTV), a human immunodeficiency virus (HIV), e.g., a long termi-nal repeat (LTR) promoter from HIV, a Moloney virus, a cytomegalovirus (CMV), an Epstein-Barr virus (EBV), and a Rous sarcoma virus (RSV), but also a β-actin promoter and promoters derived from human hemoglobin, human muscle creatine, and human metallothionein may be used, without being limited thereto.

Also, the expression vector may include a selective marker to select a host cell including a vector. The selective marker is used to select cells transformed with the vector, and markers providing selectable phenotypes such as drug resistance, auxotrophy, tolerance to cytotoxic agents, or expression of surface proteins may be used. Since only cells expressing the selection marker are able to survive in an environment treated with a selective agent, it is possible to select the transformed cells. In addition, when the vector is a replicable expression vector, the vector may include a replication origin that is a certain nucleotide sequence from which replication is initiated.

As the recombinant expression vector for insertion of a foreign gene, various types of vectors such as a plasmid, a virus, and a cosmid may be used. Any type of the recom-binant vector may be used without limitation as long as the vector may function to express a desired gene in various host cells such as prokaryotic cells and eukaryotic cells and produce a desired protein. However, a vector, which includes a promoter having strong activities and is able to mass-produce a foreign protein having a shape similar to that of the wild type while retaining a strong expression intensity, may be preferably used as the recombinant vector.

In order to express the anti-OSCAR antibody or a frag-ment thereof according to the present invention, various combinations of hosts and vectors may be used. The expres-sion vector suitable for eukaryotic hosts may contain an expression regulatory sequence derived from SV40, a bovine papilloma virus, an adenovirus, an adeno-associated virus, a cytomegalovirus, and a retrovirus without being limited thereto. The expression vector that may be used in a bacterial host includes bacterial plasmids obtained from *Escherichia coli*, such as pET, pRSET, pBluescript, pGEX2T, pUC vector, col E1, pCR1, pBR322, pMB9, and derivatives thereof; plasmids having a wide host range such as RP4; phage DNAs including various phage lambda derivatives such as λgt10, λgt11, and NM989; and other DNA phages such as M13 and filamentous single-stranded DNA phages. 2° C. plasmid or derivatives thereof may be used for yeast cells, and pVL941 may be used for insect cells.

A fifth aspect of the present invention provides a transformant other than a human including the expression vector according to the fourth aspect. The descriptions of the present invention provided above in the first to fourth aspects also apply to the transformant according to the fifth aspect of the present invention.

As used herein, the "transformant" may be a host cell to which the expression vector may be introduced. Specifically, the transformant of the present invention may be any transformant other than humans, without being limited thereto.

The host cells suitable for introduction of the vector may include prokaryotes such as *E. coli, Bacillus subtilis, Streptomyces* sp., *Pseudomonas* sp., *Proteus mirabilis*, or *Staphylococcus* sp. Also, fungi such as *Aspergillus* sp., yeast cells such as *Pichia pastoris, Saccharomyces cerevisiae, Schizosaccharomyces* sp., and *Neurospora crassa*, and other lower eukaryotes, and higher eukaryotic cells such as plant cells and insect cells may be used. Further, the host cells may be derived from mammals, specifically monkey kidney cells (COS7), NSO cells, SP2/0, Chinese hamster ovary (CHO) cells, W138, baby hamster kidney (BHK) cells, MDCK, myeloma cell lines, HuT 78 cells, and HEK293 cells, without being limited thereto.

A method for transformation of the present invention includes any method for introducing a nucleic acid into an organism, a cell, a tissue, or an organ, and transformation may be performed using standard techniques suitable for the host cell well known in the art. Specifically, electroporation, protoplast fusion, calcium phosphate (CaPO₄) precipitation, calcium chloride (CaCl₂)) precipitation, agitation using silicon carbide fibers, Agrobacteria-mediated transformation, a PEG method, a dextran sulfate method, a lipofectamine method, and drying/suppression-mediated transformation may be used without limitation.

A sixth aspect of the present invention provides a method of preparing an anti-OSCAR antibody or a fragment thereof, the method including culturing the transformant according to the fifth aspect. The descriptions of the present invention provided above in the first to fifth aspects also apply to the preparation method according to the sixth aspect of the present invention.

The method of preparing the anti-OSCAR antibody or a fragment thereof includes culturing the transformant of the present invention, specifically preparing an expression vector by inserting a polynucleotide encoding the anti-OSCAR antibody or a fragment thereof into a vector; preparing a transformant by introducing the expression vector into a host cell; culturing the transformant; and isolating and purifying the anti-OSCAR antibody or a fragment thereof from the cultured transformant.

More specifically, the transformant may be produced on a large scale by culturing the transformant in a nutrient medium, and the medium and culture conditions may be properly selected according to the host cell. The conditions such as temperature, pH of a medium, and a culture time may be properly adjusted to enable the growth of cells and mass-production of a protein.

The peptide or protein recombinantly produced as described above may be recovered from the medium or cell lysates. In the case of membrane-bound form, the peptide or protein may be separated from the membrane by using a proper surfactant solution (e.g., Triton-X 100) or via enzymatic cleavage. Cells used for expression of the anti-OSCAR antibody or a fragment thereof may be destroyed by various physical or chemical means such as freeze-thaw purification, sonication, mechanical disruption, or cytolytic agent, and may be isolated and purified by common biochemical isolation technology (Sambrook et al., *Molecular Cloning: A Laboratory Manual*, 2nd Ed., Cold Spring Harbor Laboratory Press (1989); Deuscher, M., *Guide to Protein Purification Methods Enzymology*, Vol. 182. Academic Press. Inc., San Diego, CA (1990)). Electrophoresis, centrifugation, gel filtration, precipitation, dialysis, chromatography (ion-exchange chromatography, affinity chromatography, immunosorbent chromatography, size-exclusion chromatography, and the like), isoelectric focusing, and various changes and complex methods are available, without being limited thereto.

A seventh aspect of the present invention provides a method of screening an OSCAR protein inhibitor, the method including: (a) culturing isolated chondrocytes and treating the cultured chondrocytes with a candidate substance for the OSCAR protein inhibitor; (b) treating the cultured chondrocytes with collagen; and (c) measuring an expression level of an osteoarthritis marker in the chondrocytes. The descriptions of the present invention provided above in the first to sixth aspects also apply to the screening method according to the seventh aspect of the present invention.

According to an embodiment of the present invention, the osteoarthritis marker may include at least one selected from the group consisting of hypoxia-inducible factors-2a (HIF-2a), matrix metalloproteinase 3 (MMP3), matrix metalloproteinase 13 (MMP13), and a disintegrin and metalloproteinase with thrombospondin motifs 5 (ADAMTS5).

According to an embodiment of the present invention, the isolated chondrocytes may be mouse-derived chondrocytes or human-derived chondrocytes.

As used herein, the term "candidate substance" refers to any substance expected to inhibit the activity of the OSCAR protein, specifically a substance binding to a collagen recognition site of the OSCAR protein to inhibit OSCAR protein-collagen linkage, without being limited thereto. The candidate substance may be molecules expected to inhibit binding of the OSCAR protein to collagen, such as anti-OSCAR antibodies, anti-OSCAR antibody fragments, proteins, oligopeptides, small organic molecules, polysaccharides, polynucleotides, compounds, or any combination thereof, and the candidate substance may include not only natural substances but also synthetic substances, without being limited thereto.

According to an embodiment of the present invention, the OSCAR protein inhibitor candidate substance may be an anti-OSCAR antibody or a fragment thereof.

According to an embodiment of the present invention, the method may further include determining the candidate substance as the OSCAR protein inhibitor or the anti-OSCAR antibody or a fragment thereof in the case where the expression level of an osteoarthritis marker decreases.

According to an embodiment of the present invention, the method may be a method for screening the anti-OSCAR antibody or a fragment thereof.

Another aspect of the present invention provides a composition for screening an OSCAR protein inhibitor including isolated chondrocytes and collagen.

An eighth aspect of the present invention provides a method of preventing or treating osteoarthritis, the method including administering the composition for preventing or treating osteoarthritis of the present invention to a subject. The descriptions of the present invention provided above in the first to seven aspects also apply to the method according to the eighth aspect of the present invention.

According to an embodiment of the present invention, the prevention or treatment method may be administration of the anti-OSCAR antibody or a fragment thereof.

According to an embodiment of the present invention, the prevention or treatment method may include administering the composition to a subject other than a human, without being limited thereto.

According to an embodiment of the present invention, the composition may be administered in a pharmaceutically effective amount to treat or suppress osteoarthritis. The pharmaceutically effective amount may vary according to various factors, such as severity of osteoarthritis, patient's age and body weight, characteristics and degrees of symptoms, type of current treatment, the number of treatment, dosage form, and administration route, and may easily be determined by experts in the relevant field. The composition of the present invention may be administered in combination with the above-described pharmacological or physiological components simultaneously or sequentially, or may be administered in combination with a conventional therapeutic agent sequentially or simultaneously. The composition may be administered once or multiple times. It is important to administer a minimum amount to obtain the maximum effect without adverse effects considering all of the factors described above, and the amount may easily be determined by one of ordinary skill in the art.

As used herein, the term "subject" refers to all animals including humans such as rats, mice, and livestock, in a condition in which osteoarthritis may be alleviated, suppressed, or treated by administering the composition of the present invention; or having osteoarthritis or at risk of developing osteoarthritis.

As used herein, the term "administration" refers to introduction of a predetermined substance into a subject by any suitable method, and the administration route of the composition of the present invention may be any general route as long as the composition reaches target tissue. The composition may be administered by intraperitoneal administration, intravenous administration, intramuscular administration, subcutaneous administration, intradermal administration, oral administration, topical administration, intranasal administration, intrapulmonary administration, or rectal administration, without being limited thereto. However, since proteins may be digested upon oral administration, an active ingredient of the composition for oral administration needs to be coated or formulated for protection against degradation in the stomach. Also, the composition may be administered using any device capable of delivering the active ingredient to a target cell.

A ninth aspect of the present invention provides a composition for preventing or treating a bone-related disease, including the isolated antibody or a fragment thereof according to the second aspect of the present invention. Also, as another embodiment thereof, provided is a method of preventing or treating a bone-related disease, the method including administering the composition for preventing or treating a bone-related disease into a subject. The descriptions of the present invention provided above in the first to eighth aspects also apply to the composition or method according to the ninth aspect of the present invention.

In an embodiment of the present invention, the bone-related diseases may be osteoporosis or osteopenia.

MODE FOR INVENTION

Hereinafter, the present invention will be described in more detail with reference to the following examples. However, the scope of the present invention is not limited thereto.

EXAMPLES

Example 1. Selection of Anti-OSCAR Antibody

Example 1-1. scFv Antibody Library Panning

To construct and select an anti-OSCAR antibody, two types of scFv libraries constructed using a method according to a previously disclosed document [*Mol. Cells,* 2009, 27, 225-235 and *PLoS ONE* 2015, 10(10):e0141045] were used. In the following examples, carbenicillin, which is a beta-lactam antibiotic like ampicillin, may be replaced with ampicillin.

First, the scFv library stored in the form of ER2537 or TG1 *E. coli* strain was cultured in 400 mL of a super broth (SB) medium containing carbenicillin and transfected by adding $10^{12}$ colony forming units (CFU) of a VCSM13 helper phage thereto when an absorbance at 600 nm ($OD_{600}$) reached 0.5, followed by stirring at rpm for 1 hour at 37° C. Finally, 70 μg/mL of kanamycin antibiotic was added thereto and stirred at 30° C. at 200 rpm overnight while stirring to produce a phage with scFv presented on the surface thereof. The next morning, the culture broth was centrifuged, and the phage contained in the culture broth was precipitated by adding 4% polyethyleneglycol-8000 and 3% sodium chloride, and then the precipitated phage was dissolved in 50 mL of a PBS buffer solution and re-precipitated in the same manner as described above so as to be finally dissolved in 2 mL of the PBS buffer solution. The resultant was centrifuged to remove impurities therefrom to obtain a phage scFv library. In general, $10^{13}$ CFU/mL or more of phage particles are contained in the final phage library.

Subsequently, after adding 1 mL of OSCAR-Fc diluted in PBS to have a concentration of 5 μg/mL to an immunotube to allow the protein to be adsorbed onto the surface of the immunotube, a 3% milk powder solution was added to the immunotube to protect the surface onto which OSCAR-Fc was not adsorbed. After emptying the immunotube, 1 mL of $10^{13}$ CFU of the antibody phage library dispersed in a 3% milk powder solution was added thereto for binding to the antigen. After the non-specifically bound phage was washed three times with a phosphate-buffered saline (PBST, tween20) solution, a remaining antigen-specific phage antibody was eluted using 1 mL of a 100 mM triethylamine solution.

Subsequently, the eluted phage was neutralized using 0.5 mL of a 1.0 M Tris-HCl buffer (pH 7.0), and 8.5 mL of TG1 *E. coli* ($OD_{600}$=0.5) was transfected therewith at 37° C. for 1 hour. The transfected *E. coli* was applied to a Luria-Bertani (LB) agar medium containing carbenicillin and incubated at 37° C. In this case, μL and 0.01 μL of *E. coli* were applied to an agar medium on a Petri dish having a diameter of 100 mm and used to count the number of eluted phage particles (cfu) from the number of colonies, and the remaining *E. coli* was centrifuged, suspended in a small amount of LB medium, and applied to an agar medium on a Petri dish having a diameter of 150 mm. The next day, the *E. coli* cultured on the 150 mm Petri dish was suspended in 5 mL of a super broth (SB)-carbenicillin culture medium, and glycerol was added thereto to a final concentration of 15%. A portion was stored at −80° C., and 50 µL of the rest was inoculated onto 20 mL of a SB-carbenicillin-2% glucose solution and incubated at 37° C. When the absorbance ($OD_{600}$) of the incubated culture reached 0.5, the resultant was centrifuged to isolate bacteria. The isolated bacteria were suspended in 20 mL of a SB-carbenicillin culture medium, and then $10^{11}$ PFU (plaque-forming units) of a VCSM13 helper phage was added thereto, followed by incubation while slowly stirring at 37° C.

After 1 hour of incubation, 70 µg/mL kanamycin was added thereto and incubated overnight at 30° C. while rapidly stirring (250 rpm). The next day, the culture broth was centrifuged, and then the panning process was repeated using 1 mL of a supernatant containing phage particles as a library to concentrate antigen-specific clones. The panning process was repeated five times in total, and mouse OSCAR-Fc was used as an antigen in the first, third, and fifth processes, and human OSCAR-Fc was used as an antigen in the second and fourth processes to thereby select scFv having cross-species specificity to the human and mouse OSCAR. In the first and second processes, 5 µg of the antigen was used, and 1 µg of the antigen was used thereafter.

Example 1-2. Selection of Anti-OSCAR Antibody Via ELISA Screening

To select anti-OSCAR antibodies via ELISA screening, first, 200 µL of SB-carbenicillin was added to each well of a 96-well microplate, and *E. coli* colonies obtained in the third and fourth panning processes were added thereto, followed by incubation at 37° C. for 2 hours while stirring. Using a plate replication pin tool, the cultured clones were transferred to a new microplate, IPTG was added to each well in which *E. coli* was cultured to a final concentration of 1 mM, followed by incubation at for 16 hours while stirring. Then, the microplate was centrifuged and the supernatant discarded, and then precipitated *E. coli* was suspended in 40 µL of ice-cold 1×TES (20% sucrose, 50 mM Tris, 1 mM EDTA, pH 8.0) per well. Then, µL of ice-cold 0.2×TES was added to each well, mixed well, and left on ice for 30 minutes, followed by centrifugation of the microplate to obtain a periplasm extract.

Subsequently, 25 µL of human and mouse OSCAR-Fc and human IgG each diluted in PBS to a concentration of 2 µg/mL were added to each well of a 96-well plate for ELISA and left to stand at 37° C. for 1 hour such that an antigen was adsorbed onto the surface of the well. The surface not adsorbed with the antigen was protected by applying a 3% milk powder solution and maintaining for 1 hour, and the milk powder solution was removed. 25 µL of the periplasm extract was added to each well and left to stand at room temperature for 1 hour for antigen-antibody binding. The microplate was washed three times with PBST, and 25 µL of horseradish peroxidase (HRP)-conjugated anti-HRP antibody diluted in the 3% milk powder solution to 1:3,000 was added to each well and left to stand at room temperature for 1 hour. After washing the microplate three times with PBST, 25 µL of 3,3',5,5'-tetramethylbenzidine (TMB) was added to each well to induce color development. Once a blue color was clearly developed, reaction was terminated by adding 25 µL of 1 N aqueous sulfuric acid solution to each well, and a color change signal was measured using absorbance at a wavelength of 450 nm. Human IgG was used as a control antigen to identify a clone binding to the Fc site, and clones binding to the human and mouse OSCAR-Fc without binding to the human IgG were selected by analyzing ELISA signals.

Example 1-3. scFv Antibody Sequencing

For sequencing the scFv antibody, an scFv gene showing a strong ELISA signal was amplified from the replicated microplate via PCR, and a DNA sequence was analyzed. The PCR was performed using pC3X-f (SEQ ID NO: 1) and pC3X-b (SEQ ID NO: 2) primers, and the sequence analyzing was performed using ompseq (SEQ ID NO: 3).

TABLE 1

| Sequence name | Base sequence (5'-3') | SEQ ID NO: |
|---|---|---|
| pC3X-f | GCA CGA CAG GTT TCC CGA C | 1 |
| pC3X-b | AAC CAT CGA TAG CAG CAC CG | 2 |
| ompseq | AAG ACA GCT ATC GCG ATT GCA G | 3 |

Among the analyzed scFv sequences, overlapping sequences were excluded, and a total of seven unique sequences (A1, B4, B12, C11, D2, D11, and H10) having cross-species specificity to the human and mouse OSCAR were confirmed. The clones were expressed again in 3 mL of SB-carbenicillin according to the above-described method, and a periplasm extract was obtained therefrom to re-confirm binding affinity to the human and mouse OSCAR (FIG. 1).

Example 2. Expression and Purification of Anti-OSCAR Antibody

Example 2-1. Purification of Anti-OSCAR scFv

To purify anti-OSCAR scFv, scFv *E. coli* clones were incubated while stirring in 20 mL of a SB-carbenicillin medium at 37° C. until $OD_{600}$ reached 0.5, and IPTG was added thereto to a final concentration of 1 mM, followed by incubation at 30° C. for 16 hours while stirring. Then, the culture broth was centrifuged, and precipitated cells were dispersed in 1 mL of cold 1×TES, and then 1.5 mL of cold 0.2×TES was added thereto and left to stand in ice for 30 minutes. The resultant was centrifuged to obtain a supernatant, and magnesium sulfate was added thereto to a final concentration of 5 mM. After adding 100 µL of Ni-NTA agarose beads to the extract, the resultant was incubated for 30 minutes while shaking and centrifuged to remove a supernatant. Subsequently, Ni-NTA agarose beads were washed twice with 1 mL of PBS containing 5 mM imidazole, and the bound scFv was eluted three to five times using 200 µL of PBS containing 300 mM imidazole. A concentration of the purified scFv was measured using absorbance at 280 nm, and purity thereof was analyzed via SDS-PAGE.

Example 2-2. Purification of Anti-OSCAR IgG

To purify the anti-OSCAR IgG, genes of the heavy chain variable domain (VH) and the light chain variable domain (VL) of scFv were amplified by PCR and cloned to pcIW3.3-HC and pcIW3.3-LC vectors, respectively. Information on the pcIW3.3 vector is disclosed in a master's thesis, Ewha Womans University, Seoul (Minjeong KIM, 2018, UCI identification code 1804:11048-000000148254). The heavy chain variable domain was cloned using an AfeI/NheI restriction enzyme, the lambda light chain was cloned using an AfeI/AvrII restriction enzyme. The pcIW3.3 expression vector into which the genes of the heavy chain and light chain variable domains were cloned were transfected into ExpiCHO-S cell lines, followed by incubation for 8 to 10 days, such that the IgG antibody was secreted into the culture broth.

Upon completion of the incubation, the resultant was centrifuged to obtain a supernatant containing the secreted IgG antibody, and the IgG antibody was purified by column chromatography using protein G agarose. A concentration of the purified antibody was measured using absorbance at 280 nm, and purity was analyzed via SDS-PAGE.

Example 3. Evaluation of OSCAR-Collagen Interaction Inhibitory Ability of Anti-OSCAR Antibody To identify whether the anti-OSCAR antibody prepared in the present invention inhibits OSCAR-collagen interaction, an experiment as described below was performed. Specifically, 25 µL of collagen (collagen type I from rat tail) diluted with PBS to a concentration of 2 µg/mL was added to an ELISA plate and adsorbed onto the ELISA plate by leaving to stand at 4° C. overnight. The surface onto which collagen was not adsorbed was protected by using a 3% milk powder solution. Subsequently, the purified anti-OSCAR IgG antibody and human or mouse OSCAR-Fc [fusion of ectodomain of human and mouse-derived OSCAR protein and Fc domain of human immunoglobulin gamma 1 (human IgG1)] [human-derived: hOSCAR-Fc (SEQ ID NO: 4) and mouse-derived: mOSCAR-Fc (SEQ ID NO: 5)] were mixed to have concentrations of 2 µg/mL and 1 µg/mL, respectively, for 1.5 hours to bind to each other. Then, the mixture was added to the collagen-adsorbed ELISA plate from which the powdered milk solution was removed in an amount of µL/well and left to stand at room temperature for 1.5 hours. Subsequently, the plate was washed three times with PBST to remove unreacted antibodies and OSCAR-Fc, and 25 µL of an HRP-conjugated anti-human IgG antibody diluted at 1:3,000 was added to each well and left to stand at room temperature for 1 hour to detect OSCAR-Fc bound to collagen. After the plate was washed three times with PBST, 25 µL/well of a TMB substrate was added thereto to induce blue color development, and 25 µL/well of a 1 N aqueous sulfuric acid solution was added thereto to terminate the reaction. Absorbance was measured at 450 nm to analyze the degree of OSCAR-collagen binding (FIG. 2).

As a result, it was confirmed that the novel anti-OSCAR IgG antibody developed in the present invention binds to the OSCAR protein to effectively inhibit binding between the OSCAR protein and collagen.

Example 4. Method of Screening Novel Anti-OSCAR Antibody

Example 4-1. Development of Novel Anti-OSCAR Antibody Screening Bioassay Using Chondrocytes A novel cross-linking bioassay method was developed in the present invention for screening an anti-OSCAR antibody that inhibits binding to collagen based on the fact that OSCAR is expressed in chondrocytes and the fact that expression levels of osteoarthritis markers such as hypoxia-inducible factors-2a (HIF-2a), matrix metalloproteinase 3 (MMP3), matrix metalloproteinase 13 (MMP13), and a disintegrin and metalloproteinase with thrombospondin motifs 5 (ADAMTS5) change in chondrocytes of cartilaginous tissue in a degenerative arthritis-induced mouse model.

Specifically, one day after applying chondrocytes (mouse-derived chondrocytes ATDC5 or human-derived chondrocytes C28/I2) to a cell culture plate, the plate was pre-treated with the Fc protein and an anti-OSCAR antibody candidate for 30 minutes and then treated with collagen, followed by incubation for 1 day. The cultured cells were analyzed by purifying mRNA and performing quantitative PCR to measure expression levels of OSCAR, MMP3, and MMP13. To verify the efficacy of the assay, mouse OSCAR-Fc and human OSCAR-Fc, which are known to block OSCAR-collagen binding, were used as standard substances.

In the cases of the human OSCAR-Fc (hOSCAR-Fc fusion protein), an extracellular domain of human OSCAR (amino acid 19-233) was inserted into a pVITRO1-Fc vector cloned from the Fc region of human IgG1 to prepare hOSCAR-Fc fusion DNA, and then mammalian cells (e.g., COS, CHO, BHK, 293, 3T3, and NSO cell-293F cells) were transected with the fusion DNA and cultured for 6 days. The culture medium for the cells was passed through Protein G Sepharose beads, and proteins secreted from the cells were purified using 100 mM glycine (pH 2.0) and eluted proteins were immediately neutralized by adding 1 M Tric-CI (pH 7.0) in a tube for purification. The proteins collected in the tube were dialyzed against PBS to change lysed solution, concentrated, and preserved in a cryopreserved state at −80° C. Production of the mouse OSCAR-Fc was performed in accordance with the method of producing human OSCAR-Fc.

Example 4-2. Screening of Effective Antibody Via Bioassay

As a standard substance for verifying the efficacy of the anti-OSCAR antibody, the human OSCAR-Fc (hOSCAR-Fc) protein prepared in Example 4-1 described above was used after purification. It was confirmed that the markers induced by collagen in the mouse-derived chondrocytes ATDC5 were inhibited by seven types of anti-OSCAR antibodies developed in the present invention by using the novel cross-linking bioassay developed in Example 4-1 (FIG. 3). In addition, it was confirmed that the anti-OSCAR antibodies B4, D2, and D11 selected based on the above-described results function as antagonists in expression of OSCAR-collagen induction marker in human-derived chondrocytes C28/I2 as well (FIG. 4).

Based in the above-described results, it can be seen that the novel anti-OSCAR antibody of the present invention may treat and prevent osteoarthritis induced by OSCAR protein signaling by inhibiting binding between OSCAR and collagen in chondrocytes.

Example 5. Verification of Efficacy of Anti-OSCAR Antibody in Mouse Osteoarthritis Model To identify therapeutic effects of the novel anti-OSCAR antibody developed in the present invention in a mouse osteoarthritis model, an experiment was performed as described below. First, a mouse osteoarthritis model was prepared by performing destabilization of the medial meniscus (DMM). Specifically, the medial meniscus of the right knee of a 10-week-old male mouse anesthetized by intraperitoneal injection of 2.5% avertin prior to surgery was incised with a microsurgical knife or a #11 blade. The surgery was performed on a hot pad maintained at 37° C. to prevent the body temperature of the mouse from lowering. The left knee was sham-operated as a control, and a surgical site was sutured with a suture thread.

After a recovery period of 3 to 4 days from osteoarthritis induction by the DMM surgical model as described above, the anti-OSCAR antibody developed in the present invention or the human-derived OSCAR-Fc protein, as a comparative example, was injected into the right knee that had undergone the surgery by intra-articular injection twice a week for 8 weeks. PBS was injected into the left knee that had undergone the sham surgery as a control.

For histological analysis upon completion of drug administration, the mouse was sacrificed to collect knee bones, and the collected knee bones were immobilized in 10% formaldehyde and decalcified using a 0.5 M EDTA solution having a pH of 7.4. Then, paraffin blocks prepared therefrom were cut to a thickness of 5-6 μm and stained with hematoxylin-eosin (H&E), safranin-O, and fastgreen. The severity of osteoarthritis of the stained tissue was measured according to a scoring method of the Osteoarthritis Research Society International (OARSI). Among the anti-OSCAR antibodies B4, D2, and D11, anti-OSCAR antibodies B4 and D11 having high purification rates were used.

Figure 6:
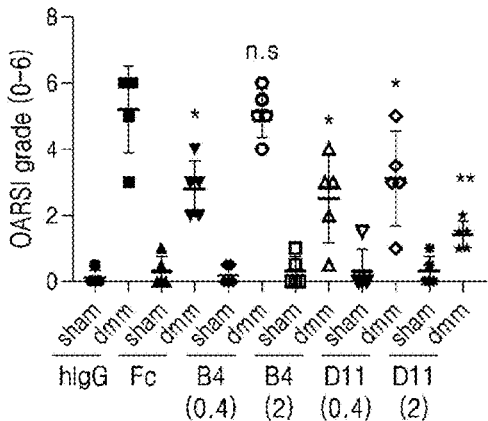
FIG. 6 shows quantitative efficacy analysis results of anti-OSCAR antibodies in an osteoarthritis model.

Based on the results of the experiment, the cartilage of the mouse injected with the anti-OSCAR antibody B4 exhibited similar inhibitory effects to those of the cartilage of the mouse injected with the OSCAR-Fc at a high concentration (2 mg/kg), and the cartilage of the mouse injected with the anti-OSCAR antibody D11 exhibited similar effects to those of the cartilage of the mouse injected with the OSCAR-Fc even at a low concentration (0.4 mg/kg). Because a significantly lower incidence of osteoarthritis was observed at a high concentration, it was histologically confirmed that the B4 and D11 antibodies inhibit incidence of osteoarthritis in the osteoarthritis mouse model (FIG. 5), and this was confirmed by quantification according to an OARSI grading method (FIG. 6).

Based on the above results, it can be seen that the novel anti-OSCAR antibody developed in the present invention, particularly clone antibodies B4 and D11, may inhibit OSCAR-collagen interaction, and osteoarthritis may be treated or prevented by way of the above-described mechanism.

The amino acid sequences of the heavy chain variable domain and the light chain variable domain of the anti-OSCAR antibody B4 are as set forth in SEQ ID NOS: 6 and 7, and the amino acid sequences of the heavy chain variable domain and the light chain variable domain of the anti-OSCAR antibody D11 are as set forth in SEQ ID NOS: 14 and 15.

Example 6. Optimization of Anti-OSCAR Antibody

Example 6-1. Development of Anti-OSCAR Antibody with Improved Affinity

Among the two types of clones (B4 and D11) confirmed to have therapeutic effects on osteoarthritis while effectively neutralizing the activity of OSCAR through the biochemical and cell-based assays and the animal model experiments as shown in the above examples, a study was conducted to improve affinity of the D11 having high efficacy. The D11 includes VH3-23(DP47) heavy chain variable domain and VL1g (IGVL1-47) lambda light chain variable domain as a scaffold.

Specifically, a study was carried out to find an optimized antibody using random mutation of CDR-H3 of the D11 clone. The CDR-H3 of the D11 clone consists of twelve amino acids. Among these, Ala-Lys (AK) at the N-terminus and Phe-Asp-Ile (FDI) at the C-terminus are sequences commonly found in the CDR-H13 of various antibodies, and thus they were not randomized, but mutation was introduced into only seven amino acids in the middle.

First, six focused libraries were constructed by introducing random mutation into two consecutive amino acid positions by using NNK codon (N=A/T/G/C and K=G/T), and these libraries were named D11-H3-1 to 6, respectively (FIG. 7A). Subsequently, in order to select antibodies with improved affinity from the libraries, panning was performed three times under the conditions of low antigen concentration and high selection pressure (increase in the number and time of washing). 1 μg/mL hOSCAR-Fc was coated in the first and second panning, and 0.2 μg/mL of hOSCAR-Fc was coated in the third panning, and then Herceptin was mixed with the libraries at a concentration of 100 μg/mL to remove the Fc-bound clones. In addition, the washing was performed five times with PBST in the first and second panning, and the washing was performed eight times with PBST and then twice with PBST for 30 minutes in the third panning. As a result, the output tended to decrease in the third panning, and this is considered to be caused by antigen concentrations and strict conditions for washing in the third panning. In addition, in the case of the D11-H3-3 library, the output titer was very low in the third panning, and it is considered that randomized amino acid positions play an important role in binding in the corresponding libraries (FIG. 7B).

Then, the output clones were screened by ELISA, and sequence analysis was performed mainly on clones having higher binding signals compared to the background (Herceptin, Fc control). As a result, a number of sequences appeared to be contamination of clones found in previous panning regardless of the D11 clone, and one clone (D11-B9) was confirmed as a CDR-H3 variant of the D11 clone from the D11-H3-4 library. In addition, by additional ELISA screening, four clones were found from D11-H3-3, one clone was found from D11-H3-4, one clone was found from D11-H3-5, and one clone was found from D11-H3-6.

Figure 8:
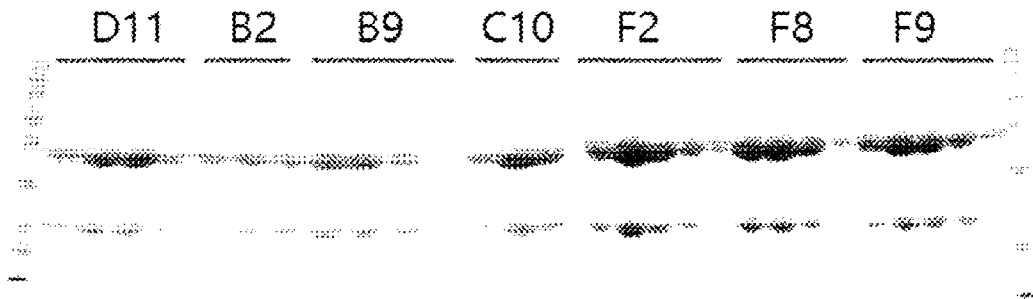
FIG. 8 shows IgG purification and SDS-PAGE results of clones that had undergone an affinity maturation process of D11.

Example 6-2. Expression, Purification, and Affinity Evaluation of Optimized Anti-OSCAR Antibody Among the clones identified via affinity maturation of the clone D11 as described above, five types were transformed with IgG and expressed and purified from the ExpiCHO-S cell line. Since these clones have the same light chain as the clone D11 and different CDR-H3 sequences of the heavy chain, only the heavy chain variable domain was cloned using a pcIW3.3-HC vector, and the expression vector of the light chain was the same as that of the D11 (FIG. 8).

Next, the $EC_{50}$ values of the clones were calculated using a 4-parameter logistic curve fit from serial dilution ELISA. As a result, it was confirmed that D11-B9 had the most superior affinity, and the $EC_{50}$ values of the clones D11, D11-B2, D11-69, D11-C10, D11-F2, D11-F8, and D11-F9 were calculated as 520 nM, 80 nM, 1.5 nM, 70 nM, 1 μM, and 250 nM, respectively (FIG. 9).

Figure 10:
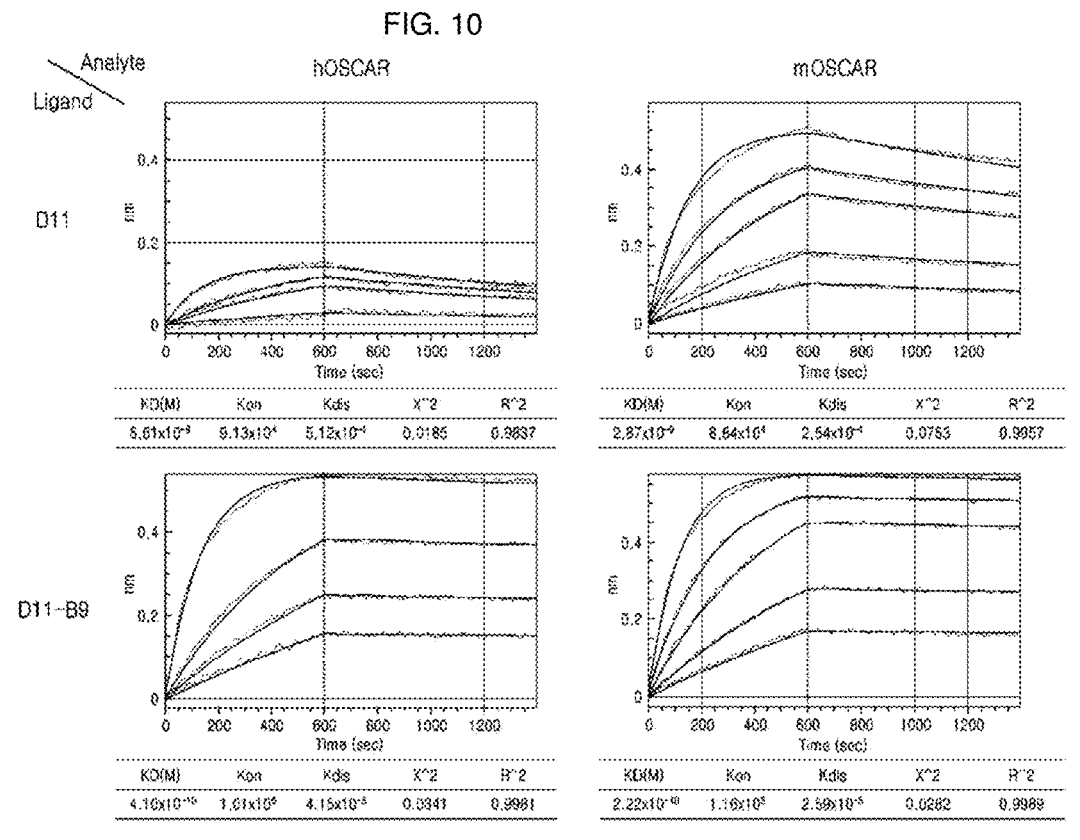

Therefore, based on intensities of the ELISA signals, expression levels, stability, and activity of the clones whose affinity was matured from the clone D11, D11-B9 was selected, and relative affinity thereof to OSCAR was re-evaluated by way of serial dilution. Specifically, the $EC_{50}$ values of the D11-B9 against hOSCAR and mOSCAR were each evaluated to be 36.8 nM. To measure a dissociation constant more accurately, analysis was performed by measuring bio-layer interferometry (BLI) signals using an Octet device. As a result, upon comparison of the clone D11 and the clone D11-B9 having matured affinity, the clone D11-B9 exhibited affinity to hOSCAR and mOSCAR by 10 times or more, and the clone D11-B9 exhibited a dissociation constant of 0.4 nM for hOSCAR and a dissociation constant of 0.2 nM for mOSCAR. In the same manner as in the serial dilution ELISA, the clone D11 seems to have a lower affinity to hOSCAR. A dissociation constant was about 5.6 nM, and a lower response signal was measured (FIG. 10).

Based on the above-described results, it was confirmed that the clone D11-B9 whose affinity was matured from the clone D11 had excellent affinity to OSCAR, and thus the clone D11-B9 selected as a final candidate substance and the mother-clone D11 were produced in the form of IgG, purified, and used for in vivo efficacy analysis.

In addition, the amino acid sequences of the heavy chain variable domain and the light chain variable domain of the anti-OSCAR antibody D11-B9 are as set forth in SEQ ID NOS: 22 and 23.

Example 6-3. Verification of Efficacy of Optimized Anti-OSCAR Antibody in Mouse Osteoarthritis Model In the same manner as in Example 5 described above, after a recovery period of 3 to 4 days from osteoarthritis induction by the DMM surgical model described above, the anti-OSCAR antibodies D11 and D11-B9 (2 mg/kg) were injected into the right knee that had undergone the surgery by intra-articular injection twice a week for 8 weeks. PBS was injected into the left knee that had undergone the sham surgery as a control. After 8 weeks, tissue was stained with hematoxylin-eosin (H&E), safranin-O, and fastgreen to measure and compare the severity of osteoarthritis according to a method used in previous studies. As a result, it was confirmed that the incidence of osteoarthritis was significantly low in cartilage of the mouse injected with D11, and D11-B9 also significantly inhibits the incidence of osteoarthritis like D11. Based on the results of the experiment, it was confirmed that the antibody D11 and the antibody D11-B9 that had undergone affinity maturation had relatively high inhibitory effects compared to the antibody B4 of Example 5 (FIG. 11A). Also, the results were also confirmed by quantitative analysis of grade classification according to a scoring method of the Osteoarthritis Research Society International (OARSI) (FIG. 11B).

In general, remodeling of a subchondral bone occurs with the progression of osteoarthritis and the thickness of the subchondral plate increases histologically. Also, while a hyaline cartilage (HC) is distributed in a wider area than a calcified cartilage (CC) in an articular cartilage in a normal case, the area of the calcified cartilage (CC) is enlarged when osteoarthritis develops. Therefore, to identify therapeutic effects of the antibodies D11 and D11-B9 on osteoarthritis, the structure of the subchondral bone was analyzed. As a result, it was confirmed that the thickness of the subchondral bone of the mouse injected with the antibody D11 was not increased when compared with the control (hIgG) in the osteoarthritis model, and the effects of the antibody D11-B9 was superior to those of the antibody D11 (FIGS. 12A and

12B). In addition, referring to HC/CC distribution, it was confirmed that the HC/CC obtained by injecting the antibodies D11 and D11-B9 was higher than that obtained by injecting the control. Thus, it was confirmed that the antibodies D11 and D11-B9 inhibit a decrease in the HC thickness caused by development of osteoarthritis. Also, it was confirmed that the antibody D11-B9 had superior inhibitory effects on the decrease in the HC thickness compared to the antibody D11 (FIG. 12C).

Example 7. Identification of Mechanism of Action of Anti-OSCAR Antibody

To identify a therapeutic mechanism (Mode-of-Action, MOA) of the anti-OSCAR antibody prepared in the present invention for treating osteoarthritis, an experiment was performed as follows. Specifically, in the same manner as in Example 6 described above, after a recovery period of 3 to 4 days from osteoarthritis induction by the DMM surgical model as described above, the anti-OSCAR antibodies D11 and D11-B9 (2 mg/kg) were injected into the right knee that had undergone the surgery by intra-articular injection twice a week for 8 weeks. PBS was injected into the left knee that had undergone the sham surgery as a control. Inhibitory effects on apoptosis thereof were identified by immunohis-tochemical staining. As a result, both of the antibodies D11 and D11-B9 reduced expression of TNF-related apoptosis-inducing ligand (TRAIL) protein, which is known to induce apoptosis, but increased expression of osteoprotegerin (OPG) protein (FIG. 13). Thus, it was confirmed that both of the antibodies D11 and D11-B9 inhibit apoptosis-associated signaling, and in particular, the inhibitory effects of the antibody D11-B9 on apoptosis signaling were superior to those of the antibody D11.

Subsequently, changes in apoptosis of chondrocytes by the anti-OSCAR antibodies were compared and analyzed via a TUNEL staining assay, which is known as a test method for identifying apoptosis. As a result, it was confirmed that both D11 and D11-B9 reduced apoptosis, and in particular, the inhibitory effects of D11-B9 on apoptosis were superior to those of D11 (FIG. 14).

Based on the results, it was confirmed that the anti-OSCAR antibodies D11 and D11-B9 had inhibitory effects on apoptosis of chondrocytes, and it is considered that these antibodies may be used as therapeutic agents for osteoar-thritis.

The above description of the present invention is provided for the purpose of illustration, and it would be understood by those skilled in the art that various changes and modifica-tions may be made without changing the technical concep-tion and essential features of the present invention. Thus, it is clear that the above-described embodiments are illustra-tive in all aspects and do not limit the present invention. For example, each component described in a singular form may be embodied in a distributed form. Likewise, components described in a distributed form may be embodied in a combined form.

Therefore, the scope of the disclosure is defined not by the detailed description, but by the claims and their equivalents, and all variations within the scope of the claims and their equivalents are to be construed as being included in the disclosure.

The invention claimed is:

1. An isolated antibody that binds to an osteoclast-associated Ig-like receptor (OSCAR) protein or a fragment thereof, wherein the antibody or a fragment thereof comprising a heavy chain variable domain and a light chain variable domain is at least one selected from the group consisting of:

1) an isolated anti-OSCAR antibody or a fragment thereof comprising a heavy chain variable domain consisting of SEQ ID NO: 6 and a light chain variable domain consisting of SEQ ID NO: 7;

2) an isolated anti-OSCAR antibody or a fragment thereof comprising a heavy chain variable domain consisting of SEQ ID NO: 14 and a light chain variable domain consisting of SEQ ID NO: 15; and 3) an isolated anti-OSCAR antibody or a fragment thereof comprising a heavy chain variable domain consisting of SEQ ID NO: 22 and a light chain variable domain consisting of SEQ ID NO: 23.

2. A composition for preventing or treating a bone-related disease, comprising the isolated antibody or a fragment thereof of claim 1, wherein the bone-related disease is osteoporosis or osteopenia.

3. A method of preventing or treating osteoarthritis, the method comprising administering the isolated antibody or a fragment thereof according to claim 1 to a subject.

* * * * *